United States Patent
Ganesan et al.

(10) Patent No.: US 9,889,081 B2
(45) Date of Patent: Feb. 13, 2018

(54) ALDEHYDE DEHYDROGENASE INHIBITORS AS NOVEL DEPIGMENTING AGENTS

(71) Applicants: The Regents of the University of California, Oakland, CA (US); Board of Regents, The University of Texas System, Austin, TX (US)

(72) Inventors: Anand Ganesan, Ladera Ranch, CA (US); Michael A. White, Dallas, TX (US); Patrick J. Farmer, Waco, TX (US)

(73) Assignees: The Regents of the University of California, Oakland, CA (US); Board Of Regents, The University Of Texas System, Austin, TX (US)

( * ) Notice: Subject to any disclaimer, the term of this patent is extended or adjusted under 35 U.S.C. 154(b) by 168 days.

(21) Appl. No.: 14/322,837

(22) Filed: Jul. 2, 2014

(65) Prior Publication Data
US 2014/0314698 A1 Oct. 23, 2014

Related U.S. Application Data

(62) Division of application No. 13/598,499, filed on Aug. 29, 2012, now Pat. No. 8,802,733, which is a division of application No. 12/587,010, filed on Sep. 29, 2009, now abandoned.

(60) Provisional application No. 61/100,989, filed on Sep. 29, 2008.

(51) Int. Cl.
| | | |
|---|---|---|
| *A61K 8/42* | (2006.01) | |
| *A61K 31/26* | (2006.01) | |
| *A61K 8/46* | (2006.01) | |
| *A61K 47/16* | (2006.01) | |
| *A61K 31/27* | (2006.01) | |
| *A61K 31/145* | (2006.01) | |
| *A61K 31/275* | (2006.01) | |
| *A61K 8/41* | (2006.01) | |
| *A61Q 19/02* | (2006.01) | |
| *A61K 8/40* | (2006.01) | |
| *A61K 31/16* | (2006.01) | |

(52) U.S. Cl.
CPC ............... *A61K 8/46* (2013.01); *A61K 8/40* (2013.01); *A61K 8/41* (2013.01); *A61K 8/42* (2013.01); *A61K 31/145* (2013.01); *A61K 31/26* (2013.01); *A61K 31/27* (2013.01); *A61K 31/275* (2013.01); *A61K 47/16* (2013.01); *A61Q 19/02* (2013.01); *A61K 31/16* (2013.01)

(58) Field of Classification Search
None
See application file for complete search history.

(56) References Cited

U.S. PATENT DOCUMENTS

| 4,713,078 A | 12/1987 | David et al. |
|---|---|---|
| 6,093,419 A * | 7/2000 | Rolf ............... A61K 9/703 424/448 |
| 6,120,806 A | 9/2000 | Whitmire |
| 2003/0114475 A1* | 6/2003 | Fox ............... A61K 31/145 514/282 |
| 2003/0119715 A1* | 6/2003 | Ward ............... A61K 31/10 514/1 |
| 2003/0229064 A1 | 12/2003 | Kennedy |
| 2006/0149061 A1 | 7/2006 | Anli et al. |
| 2010/0227920 A1 | 9/2010 | Ganesan et al. |
| 2013/0101535 A1 | 4/2013 | Ganesan et al. |

OTHER PUBLICATIONS

Zathurecky et al., Evaluation of the action of antioxidants on the stability of salve bases with animal and plant fats by application of the accelerated method of active oxygen, 1961, Cesko-Solvenska Farmacie, vol. 10(10), pp. 497-506, Abstract Only.*
US Office Action (Restriction Requirement) dated Dec. 2, 2011 issued in U.S. Appl. No. 12/587,010.
US Office Action dated Apr. 2, 2012 issued in U.S. Appl. No. 12/587,010.
US Office Action dated Aug. 2, 2013 issued in U.S. Appl. No. 13/598,499.
US Notice of Allowance dated Apr. 2, 2014 issued in U.S. Appl. No. 13/598,499.
Ando et al. (2007) "Approaches to identify inhibitors of melanin biosynthesis via the quality control of tyrosinase." *J Invest Dermatol* 127(4): 751-761.
Barsh (2003) "What controls variation in human skin color?" PLoS Biol 1(1): E27, pp. 19-22.
Bennett et al. (2003) "The color loci of mice—a genetic century." *Pigment Cell Res* 16(4): 333-344.
Cen et al. (2002) "Disulfiram induces apoptosis in human melanoma cells: a redox-related process." *Mol Cancer Ther* 1(3): 197-204.
Costin et al. (2007) "Human skin pigmentation: melanocytes modulate skin color in response to stress." *Faseb J* 21(4): 976-994.
Dell'Angelica (2003) "Melanosome biogenesis: shedding light on the origin of an obscure organelle." *Trends Cell Biol* 13(10): 503-506.
DeMaster et al. (1998) "Mechanisms of inhibition of aldehyde dehydrogenase by nitroxyl, the active metabolite of the alcohol deterrent agent cyanamide." *Biochem Pharmacol* 55 (12): 2007-2015.
Di Pietro et al. (2006) "BLOC-1 interacts with BLOC-2 and the AP-3 complex to facilitate protein trafficking on endosomes." *Molecular biology of the cell* 17(9): 4027-4038.
Edenberg (2007) "The genetics of alcohol metabolism: role of alcohol dehydrogenase and aldehyde dehydrogenase variants." *Alcohol Res Health* 30(1): 5-13.

(Continued)

*Primary Examiner* — Jeffrey S Lundgren
*Assistant Examiner* — Meghan Finn
(74) *Attorney, Agent, or Firm* — Emily M. Haliday; Weaver Austin Villeneuve & Sampson LLP

(57) ABSTRACT

The present invention provides methods and compositions for reducing pigmentation.

8 Claims, 17 Drawing Sheets

(56) References Cited

OTHER PUBLICATIONS

Fedorow et al. (2005) "Neuromelanin in human dopamine neurons: comparison with peripheral melanins and relevance to Parkinson's disease." *Progress in neurobiology* 75(2): 109-124.
Ganesan et al. (2008) "Genome-Wide siRNA-Based Functional Genomics of Pigmentation Identifies Novel Genes and Pathways That Impact Melanogenesis in Human Cells" *PLoS Genet* 4(12): e1000298 pp. 1-23, doi:10.1371/journal.pgen.1000298.
Garraway et al. (2005) "Integrative genomic analyses identify MITF as a lineage survival oncogene amplified in malignant melanoma." *Nature* 436 (7047): 117-122.
Gillbro et al. (2011) "The melanogenesis and mechanisms of skin-lightening agents—existing and new approaches," *International Journal of Cosmetic Science* 33:210-221.
Hall et al. (2005) "Degradation of tyrosinase induced by phenylthiourea occurs following Golgi maturation." *Pigment Cell Res* 18(2): 122-129.
Hoek et al. (2004) "Expression profiling reveals novel pathways in the transformation of melanocytes to melanomas." *Cancer research* 64(15): 5270-5282.
Kim et al. (2005) "Tyrosinase inhibitors from natural and synthetic sources: structure, inhibition mechanism and perspective for the future." *Cell Mol Life Sci* 62(15): 1707-1723.
Kobayashi et al. (1994) "The Pmel 17/silver locus protein. Characterization and investigation of its melanogenic function." *J Biol Chem* 269(46): 29198-29205.
Kushimoto et al. (2001) "A model for melanosome biogenesis based on the purification and analysis of early melanosomes." *Proceedings of the National Academy of Sciences of the United States of America* 98(19): 10698-10703.
Lamason et al. (2005) "SLC24A5, a putative cation exchanger, affects pigmentation in zebrafish and humans". *Science* 310(5755): 1782-1786.
Levitt J (2007) "The safety of hydroquinone: a dermatologist's response to the 2006 Federal Register." *J Am Acad Dermatol* 57(5): 854-872.
Levy et al. (2006) "MITF: master regulator of melanocyte development and melanoma oncogene." *Trends Mol Med* 12(9): 406-414.
Malo et al. (2006) "Statistical practice in high-throughput screening data analysis." *Nat Biotechnol* 24(2): 167-175.
MMWR (2005) "Update: Hydrogen Cyanamide-Related Illnesses—Italy, 2002-2004," published 2005, *MMWR*, 54(16):405-408.
Proikas-Cezanne et al. (2004) "WIPI-1alpha (WIPI49), a member of the novel 7-bladed WIPI protein family, is aberrantly expressed in human cancer and is linked to starvation-induced autophagy." *Oncogene* 23(58): 9314-9325.
Qu et al. (2003) "Promotion of tumorigenesis by heterozygous disruption of the beclin 1 autophagy gene." *The Journal of clinical investigation* 112 (12): 1809-1820.
Raposo et al. (2007) "Lysosome-related organelles: driving post-Golgi compartments into specialisation." *Current opinion in cell biology* 19(4): 394-401.
Raposo et al. (2007) "Melanosomes—dark organelles enlighten endosomal membrane transport." *Nature reviews* 8(10): 786-797.
Sarangarajan et al. (2005) "Melanization and phagocytosis: implications for age related macular degeneration." *Molecular vision* 11: 482-490.
Sarkar et al. (2013) "Cosmeceuticals for Hyperpigmentation: what is available?," *Journal of Cutaneous and Aesthetic Surgery* 6(1):1-11.
Slominski et al. (2004) "Melanin pigmentation in mammalian skin and its hormonal regulation." *Physiol Rev* 84(4): 1155-1228.
Smit et al. (1997) "Melanogenesis in cultured melanocytes can be substantially influenced by L-tyrosine and L-cysteine." *The Journal of investigative dermatology* 109(6): 796-800.
Smit et al. (1998) "Variations in melanin formation by cultured melanocytes from different skin types." *Archives of dermatological research* 290(6): 342-349.
Smith et al. (2000) "Human Skin Absorption and Metabolism of the Contact Allergens, Cinnamic Aldehyde, and Cinnamic Alcohol" Toxicoloy and Applied Pharmacology 168: 189-199.
Stevens et al. (1996) "Pigments and Minerals" *In: JD Bancroft and A Stevens, Editors, Theory and Practical Histological Techniques*: Chapter 12: 243-267.
Sulem et al. (2007) "Genetic determinants of hair, eye and skin pigmentation in Europeans." *Nat Genet* 39(12): 1443-1452.
Tachibana (1999) "Sound needs sound melanocytes to be heard." *Pigment cell research* 12 (6): 344-354.
Theos et al. (2005) "Functions of adaptor protein (AP)-3 and AP-1 in tyrosinase sorting from endosomes to melanosomes." *Molecular biology of the cell* 16 (11): 5356-5372.
Theos et al. (2006) "A lumenal domain-dependent pathway for sorting to intralumenal vesicles of multivesicular endosomes involved in organelle morphogenesis." *Developmental cell* 10(3): 343-354.
Watabe et al. (2004) "Regulation of tyrosinase processing and trafficking by organellar pH and by proteasome activity." *The Journal of biological chemistry* 279(9): 7971-7981.
Whitehurst et al. (2007) "Synthetic lethal screen identification of chemosensitizer loci in cancer cells." *Nature* 446(7137): 815-819.
Zecca et al. (2006) "A proposed dual role of neuromelanin in the pathogenesis of Parkinson's disease." *Neurology* 67(Suppl 2): S8-11.
Zhu et al. (2002) "Neurofibromas in NF1: Schwann cell origin and role of tumor environment." *Science* 296(5569): 920-922.

\* cited by examiner

+/+
Fontana-Masson

+/-
Fontana-Masson

+/+
S100

+/-
S100

ALDEHYDE DEHYDROGENASE INHIBITORS AS NOVEL DEPIGMENTING AGENTS

CROSS-REFERENCE TO RELATED APPLICATIONS

This application is a divisional of U.S. application Ser. No. 13/598,499, filed Aug. 29, 2012, which is a divisional of U.S. application Ser. No. 12/587,010, filed Sep. 29, 2009, which claims priority to and benefit of U.S. Ser. No. 61/100,989, filed on Sep. 29, 2008, all of which are hereby incorporated by reference in their entireties, for all purposes.

STATEMENT AS TO RIGHTS TO INVENTIONS MADE UNDER FEDERALLY SPONSORED RESEARCH AND DEVELOPMENT

This invention was made with government support under NIH grant no. CA71443, National Cancer Institute grant no. P30CA62203, Laser Microbeam Program grant no. P41-RR01192, and DoD grant no. W81XWH060749. The Government has certain rights in the invention.

FIELD OF THE INVENTION

The present invention relates to generally to the treatment of hyperpigmentary skin disorders. In particular, the invention relates to methods and compositions for treating such disorders.

BACKGROUND OF THE INVENTION

Melanin protects the skin and eyes from the harmful effects of UV irradiation, protects neural cells from toxic insults, and is required for sound conduction in the inner ear. Aberrant regulation of melanogenesis underlies skin disorders (melasma and vitiligo), neurologic disorders (Parkinson's disease), auditory disorders (Waardenburg's syndrome), and opthalmologic disorders (age related macular degeneration). Much of the core synthetic machinery driving melanin production has been identified, however, the spectrum of gene products participating in melanogenesis in different physiological niches is poorly understood.

SUMMARY OF THE INVENTION

In certain embodiments, the invention provides a method for reducing skin pigmentation, the method comprising topically administering an effective amount of an inhibitor of aldehyde dehydrogenase to pigmented skin of a subject. In variations of such embodiments, the aldehyde dehydrogenase inhibitor includes disulfuram, cyanamide, or a derivative of either. In illustrative embodiments, the skin pigmentation includes hyperpigmentation, such as that due to sun exposure, inflammation, chemical exposure and/or skin trauma. Subjects amenable to treatment using such methods include those having solar lentigines, Addison's disease, Cushing's disease, Acanthosis nigricans, Melasma, Linea nigra, Peutz-Jeghers syndrome, Smoker's melanosis, Celiac disease, Cronkite-Canada syndrome, and/or Tinea fungal infection.

In other embodiments, the invention provides a topical formulation for reducing skin pigmentation, the formulation comprising an inhibitor of aldehyde dehydrogenase in a formulation selected from the group consisting of a cream, an ointment, a paste, a lotion, a gel, and a solution.

BRIEF DESCRIPTION OF THE DRAWINGS

FIG. 1A-C. Validation of novel gene products supporting melanogensis. a, MNT-1 cells were transfected with the indicated siRNA pools (50 nM final concentration) targeting 35 of the 93 positive regulators of melanogenesis identified in the primary screen. siRNAs targeting Ker7, a gene that does not impact pigment production, were used as a negative control (black bar). A normalized percent inhibition calculation (Malo et al. 2006) was employed to compare the consequences of each siRNA pool on pigmentation with that observed upon depletion of tyrosinase. Bars represent mean and s.e.m. for n=3. Red bars indicate failure to significantly suppress pigmentation. b, A light micrograph of a representative opaque-walled, clear-bottomed 96-well microtiter plate containing MNT-1 cell monolayers 7 days post transfection with the indicated siRNAs is shown. c, Four independent siRNAs targeting the indicated genes were separately tested for the capacity to suppress pigmentation as in a.

DETAILED DESCRIPTION

Figure 1A:
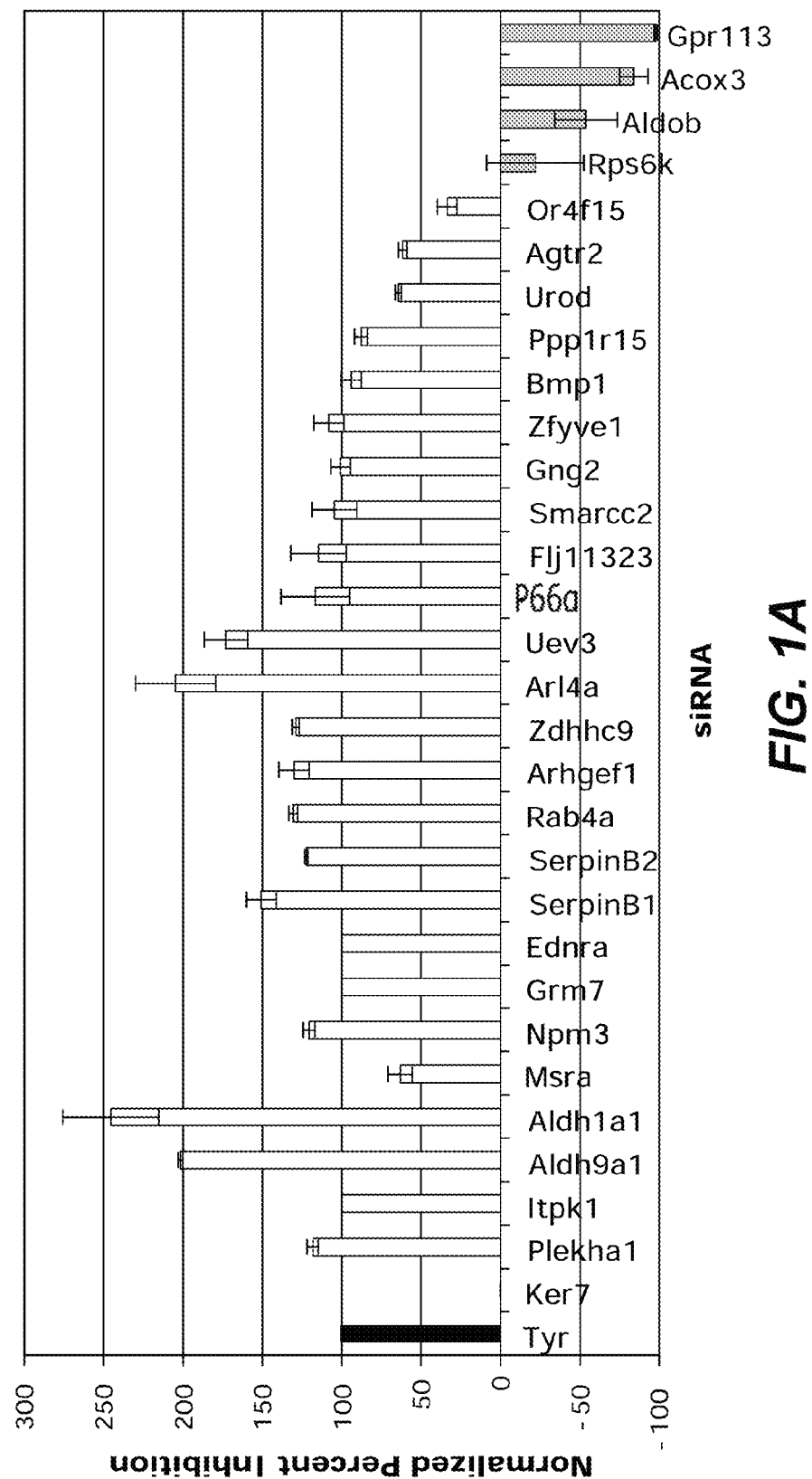
Figure 1B:
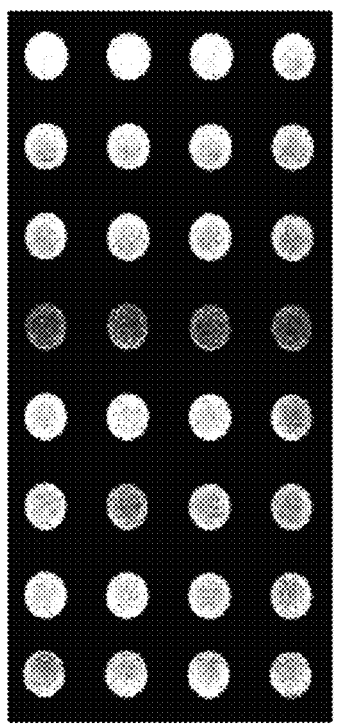
Figure 1B:
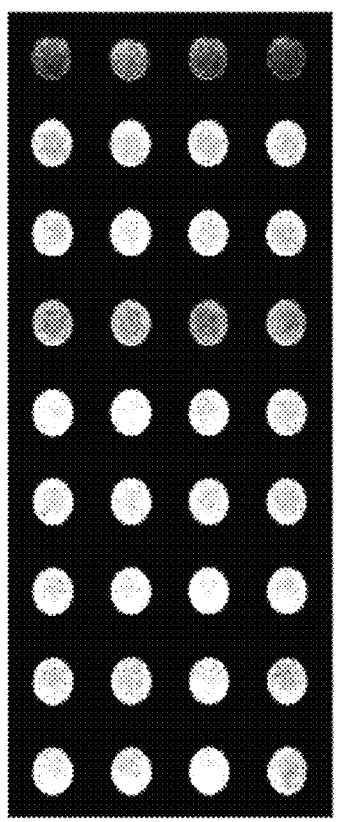

In certain embodiments, the present invention provides methods and compositions employing an aldehyde dehydrogenase inhibitor to reduce skin pigmentation.

Definitions

Terms used in the claims and specification are defined as set forth below unless otherwise specified.

The term "effective amount" is used herein to refer to an amount of an agent that is sufficient to reduce skin pigmentation.

As used with respect to a particular agent, the term "derivative" refers to any salt, ester, amide, prodrug, or other derivative of the agent, that has at least one pharmacological effect of any such compound that renders it useful in one or more of the methods of the invention, and is pharmaceutically acceptable.

An "inhibitor" or "antagonist" of a polypeptide is an agent that reduces, by any mechanism, any action or function of the polypeptide, as compared to that observed in the absence (or presence of a smaller amount) of the agent. An inhibitor of a polypeptide can affect: (1) the expression, mRNA stability, protein trafficking, modification (e.g., phosphorylation), or degradation of a polypeptide, or (2) one or more of the normal action or functions of the polypeptide. An inhibitor of a polypeptide can be non-selective or selective. Illustrative inhibitors (antagonists) are generally small molecules that act directly on, and are selective for, the target polypeptide.

I. Methods for Reducing Skin Pigmentation

A. In General

In particular embodiments, the invention provide a method for reducing skin pigmentation. The method entails topically administering an effective amount of an inhibitor of aldehyde dehydrogenase to pigmented skin of a subject.

B. Aldehyde Dehydrogenase Inhibitors

Aldehyde dehydrogenases are a group of enzymes that catalyse the oxidation (dehydrogenation) of aldehydes. Aldehyde dehydrogenase inhibitors (i.e., "active agents") suitable for use in the invention include those that inhibit the Aldh1, Aldh2, Aldh 3, and Aldh9 isozymes. Examples of aldehyde hydrogenase inhibitors suitable for use in the invention include disulfuram, cyanamide, diethyldithiocarbamate, phenethyl isothiocyanate (PEITC), daidzin (i.e., the 7-glucoside of 4',7-dihydroxyisoflavone), prunetin (4',5-dihydroxy-7-methoxyisoflavone), 5-hydroxydaidzin (genistin), Angeli's salt, and derivatives of any of these.

The active agent(s) can be administered in the "native" form or, if desired, in the form of salts, esters, amides, prodrugs, derivatives, and the like, provided the salt, ester, amide, prodrug, or derivative is suitable pharmacologically, i.e., effective in the present method. Salts, esters, amides, prodrugs, and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Pharmaceutically acceptable salts of the compounds described herein include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicyclic, succinic, gluconic, isethionic, glycinic, malic, mucoic, glutammic, sulphamic, ascorbic acid; toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to alkali such as sodium and ammonium.

For example, acid addition salts are prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Illustrative acid addition salts of the active agents herein are halide salts, such as may be prepared using hydrochloric or hydrobromic acids. Conversely, basic salts of the active agents described herein are prepared in a similar manner using a pharmaceutically acceptable base such as sodium hydroxide, potassium hydroxide, ammonium hydroxide, calcium hydroxide, trimethylamine, or the like. Illustrative basic salts include alkali metal salts, e.g., the sodium salt, and copper salts.

Acid addition salts useful in the methods described herein include the physiologically compatible acid addition salts, most preferably the dihydrochloride. Bis-quaternary salts useful in the methods described herein include the physiologically compatible bis-quaternary salts, such as the methiodide and the dimethiodide.

Preparation of esters typically involves functionalization of hydroxyl and/or carboxyl groups and/or other reactive groups that may be present within the molecular structure of the drug. The esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides and prodrugs can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine. Prodrugs are typically prepared by covalent attachment of a moiety that results in a compound that is therapeutically inactive until modified by an individual's metabolic system.

When active agents described herein contain chiral or prochiral centres they can exist in different stereoisomeric forms including enantiomers of (+) and (−) type or mixtures of them. The present invention includes in its scope both the individual isomers and the mixtures thereof.

It will be understood that, when mixtures of optical isomers are present, they may be separated according to the classic resolution methods based on their different physicochemical properties, e.g. by fractional crystallization of their acid addition salts with a suitable optically active acid or by the chromatographic separation with a suitable mixture of solvents.

C. Subjects

The methods described herein can be carried using any suitable subject, typically a mammal, and more typically, a human having skin pigmentation. In certain embodiments, the skin pigmentation is hyperpigmentation. Hyperpigmentation treatable by the methods described herein can be due to sun exposure, inflammation, chemical exposure, and/or skin trauma. In particular embodiments, the subject has a disease or disorder characterized by hyperpigmentation, such as, e.g., solar lentigines, Addison's disease, Cushing's disease, Acanthosis nigricans, Melasma, Linea nigra, Peutz-Jeghers syndrome, Smoker's melanosis, Celiac disease, Cronkite-Canada syndrome, and Tinea fungal infection.

D. Administration

In certain embodiments, aldehyde hydrogenase inhibitors are administered topically. Suitable dosage forms include, but are not limited to, a cream, an ointment, a paste, a lotion, a gel, and a solution, each of which is discussed further below.

E. Dose

Generally, the formulations described herein are administered to a subject in an amount sufficient to reduce pigmentation. Single, but more typically, multiple applications of the formulations may be administered depending on the dosage and frequency as required and tolerated by the subject.

The concentration of active agent(s) can vary and will be selected based upon the subject's needs. In accordance with standard practice, the clinician can titer the dosage to obtain the optimal effect. Generally, the clinician begins with a low dose and increases the dosage until the desired therapeutic effect is achieved. Starting doses for a given active agent can, for example be extrapolated from in vitro and/or animal data.

II. Topical Aldehyde Dehydroenase Inhibitor Formulations

In particular embodiments, the invention provides a topical formulation for reducing skin pigmentation. The formulation includes one or more inhibitors of aldehyde dehydrogenase (i.e., "active agents"), as described above, in a topical formulation. In specific embodiments, the topical formulation is a cream, an ointment, a paste, a lotion, a gel, or a solution. Topical formulations are described in Remington's Pharmaceutical Sciences (1980) 16th editions, Osol, ed., 1980, which is hereby incorporated by reference for its disclosure of topical formulations.

Creams containing the selected active agent, are typically viscous liquid or semisolid emulsions, often either oil-in-water or water-in-oil. Cream bases are typically water-washable and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

Ointments are semisolid preparations, which are typically based on petrolatum or other petroleum derivatives. The specific ointment or cream base to be used, as will be appreciated by those skilled in the art, is one that will provide for optimum drug delivery. As with other carriers or vehicles, an ointment base is preferably inert, stable, non-irritating, and nonsensitizing.

Pastes are soft, plastic mixtures or compositions that typically have a stiffer consistency than ointments and are typically less greasy because of a higher percentage of one or more powdered ingredient(s). Pastes include absorptive powders dispersed in petrolatum or hydrophilic petrolatum. Lotions are liquid, usually aqueous, preparations, generally containing one or more insoluble substance. Gels are semi-solid systems of either suspensions made up of small inorganic particles or large organic molecules interpenetrated by a liquid. Where the gel mass consists of a network of small discrete particles, the gel is classified as a two-phase system. Single-phase systems consist of organic macromolecules distributed uniformly throughout a liquid in such a manner that no apparent boundaries exist between the dispersed molecules and the liquid. Although gels are commonly aqueous, alcohols and oils can be used as a continuous phase. Solutions are liquid, usually aqueous, preparations that contain one or more soluble substances.

The active agents described herein can be combined with a pharmaceutically acceptable carrier (excipient), such as are described in Remington's Pharmaceutical Sciences (1980) 16th editions, Osol, ed., 1980, which is hereby incorporated by reference for its disclosure of carriers useful in topical formulations. Pharmaceutically acceptable carriers can contain one or more physiologically acceptable compound(s) that act, for example, to stabilize the composition or to increase or decrease the absorption of the active agent(s). A pharmaceutically acceptable carrier suitable for use in the methods described herein is non-toxic to cells, tissues, or subjects at the dosages employed, and can include a buffer (such as a phosphate buffer, citrate buffer, and buffers made from other organic acids), an antioxidant (e.g., ascorbic acid), a low-molecular weight (less than about 10 residues) peptide, a polypeptide (such as serum albumin, gelatin, and an immunoglobulin), a hydrophilic polymer (such as polyvinylpyrrolidone), an amino acid (such as glycine, glutamine, asparagine, arginine, and/or lysine), a monosaccharide, a disaccharide, and/or other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

Other pharmaceutically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) (here, topical) and on the particular physio-chemical characteristics of the active agent(s).

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLE

The following example is offered to illustrate, but not to limit, the claimed invention.

Example 1

Genome-Wide siRNAi-Based Functional Genomics of Pigmentation Identifies Novel Regulatory Networks Governing Melanogenesis in Human Cells Abstract RNA-mediated interference (RNAi)-based functional genomics provides the opportunity to derive unbiased comprehensive collections of pharmaceutically tractable single gene targets supporting melanin production. In this study, we have combined a high-throughput cell-based one-well/one-gene screening platform with a genome-wide arrayed synthetic library of chemically synthesized small interfering RNAs to identify novel biological pathways that govern melanin biogenesis in human melanocytes. 94 novel genes that support pigment production were identified with a low false discovery rate. Secondary validation and mechanistic studies identified a large panel of targets that converge on tyrosinase expression and stability. Small molecule inhibition of a family of gene products in this class was sufficient to impair chronic tyrosinase expression in pigmented melanoma cells and UV-induced tyrosinase expression in primary melanocytes. Isolation of molecular machinery known to support autophagosome biosynthesis from this screen, together with in vitro and in vivo validation, exposed a close functional relationship between melanogenesis and autophagy. Finally, isolation of loci associated with human disease suggests novel cellular processes required for melanosome formation can be attributed to components of disease pathology.

Summary

Aberrant pigment regulation correlates with skin disorders, opthalmologic disorders, and neurologic disorders. Significant effort has been focused on identifying the key molecular regulators of pigment production in mouse skin (Costin and Hearing 2007). To date, 127 mouse coat color genes have been identified, and many of these genes also impact pigment production in human skin (Bennett and Lamoreux 2003). Direct identification of genes that regulate pigment production in human skin has been hampered by the low level of melanin produced by melanocytes in tissue culture (Smit et al. 1997; Smit et al. 1998) and the limited passage life of these cells. In order to circumvent these limitations to give a broader picture of the molecular regulators of melanogenesis in human cells, we used a genome wide siRNAi functional genomics approach to identify novel regulators of melanogenesis in heavily pigmented, MNT-1 melanoma cells. Using this approach we identified 94 novel regulators of melanin production in MNT-1 cells. Secondary validation of gene targets revealed that our screening approach had a low false positive and off-target rate and accurately identified a number of genes that converge to regulate tyrosinase, the rate limiting step in pigment production in both MNT-1 cells and primary melanocytes. Small molecule inhibition of a family of gene products in this class was sufficient to impair pigment production in melanocytes. Our screening approach additionally identified molecular machinery known to support autphagosome biosynthesis. In vitro colocalization studies and autophagy deficient mice provide evidence that normal melanogenesis requires the same molecular machinery utilized by the autophagy pathway. Taken together, these results illustrate the utility of genome wide siRNA screening for identifying novel pharmacologic agents and pathways that regulate a differentiated cellular phenotype.

Introduction

Significant effort has been focused on identifying the molecular etiology for pigment variation in skin (Costin and Hearing 2007). 127 mouse coat color genes have been identified (Bennett and Lamoreux 2003), 68 of these genes have human homologues, and 29 of these homologues impact pigmentation in humans. Genetic mapping studies have identified a limited set of genes responsible for skin and eye color variability (Sulem et al. 2007). Pigment production involves the concerted actions of transcriptional, translational, and intracellular trafficking machinery (Slominski et al. 2004). MITF, the master regulator of melanogenesis in the mouse hair follicle (Levy et al. 2006), activates the transcription of tyrosinase, the rate limiting step in melanogenesis (Levy et al. 2006). Tyrosinase is translated in the endoplasmic reticulum and is glycosylated in the Golgi apparatus (Ando et al. 2007). Tyrosinase activity is restricted to the melanosome, a melanin specific organelle of poorly defined origin (Dell'Angelica 2003; Raposo and Marks 2007). While the subtle variation in human skin color is thought to be the result of the complex interaction of multiple genes, the majority of mouse mutants described have segmental or complete absence of pigment (Barsh 2003). Recent studies have identified partial loss of function mutations that impact the shade of melanin in zebrafish and human skin (Lamason et al. 2005), but the spectrum of gene targets that regulate pigment shade is unknown. Melanin is expressed in different end organs conferring different functions. Melanin protects the skin, eyes (Costin and Hearing 2007), and brain from toxic insults (Fedorow et al. 2005). Melanin in the inner ear impacts sound conduction (Tachibana 1999). Loss of melanin is thought to play a role in the etiology of age related macular degeneration (Sarangarajan and Apte 2005) and Parkinson's disease (Zecca et al. 2006). Aberrant regulation of melanin is linked to growth transformation as MITF is a lineage dependent oncogene (Garraway et al. 2005). Additionally, melanin is dysregulated in human skin disorders such as vitiligo and melasma. Harnessing the molecular mechanisms that regulate melanogenesis to selectively modulate melanin production in the skin, eye, or brain could lead to novel treatments for multiple human pathologies. Pharmacologic modulation of melanin production has primarily focused on identifying inhibitors of tyrosinase, the rate limiting step in pigment production (Kim and Uyama 2005). Currently utilized tyrosinase inhibitors are clinically effective, but are carcinogenic in animal studies (Levitt 2007). Pharmacologic agonists that stimulate pigmentation in human tissues remain to be identified. A better understanding of the molecular network governing pigment production in the human epidermis is indicated to aid design of agents that inhibit or stimulate pigmentation in human skin.

Results and Discussion

Figure 4A:
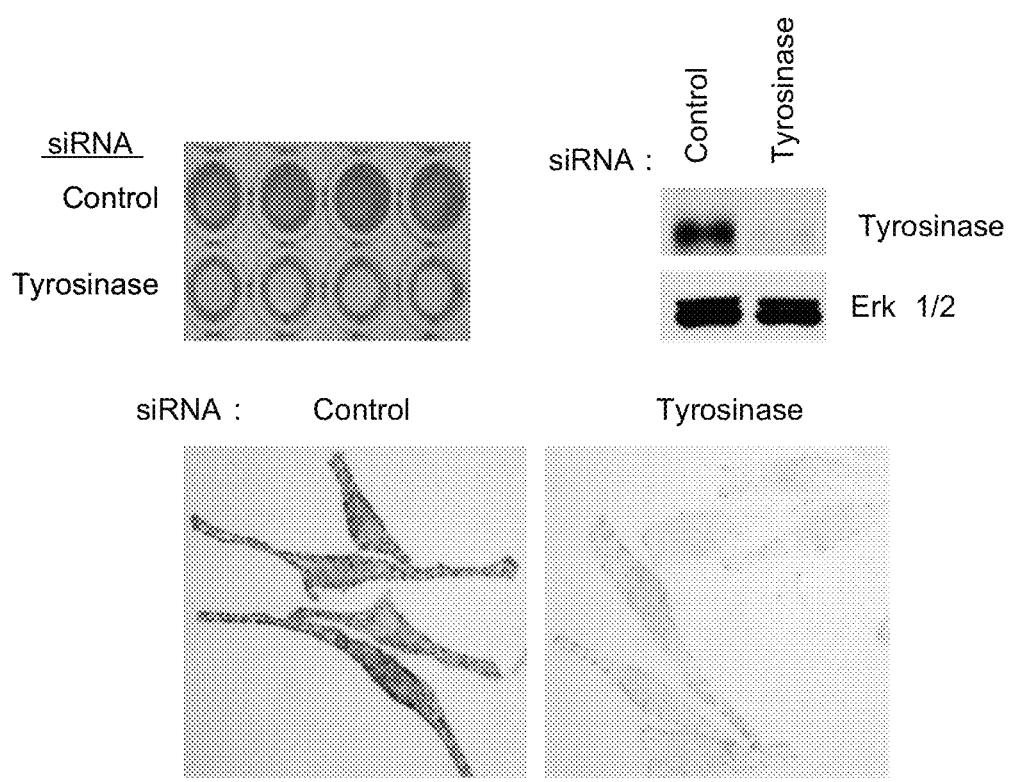
FIG. 4A-B. Genome-wide sRNAi screening for novel molecular components of melanogenesis. a, A MNT-1 model for loss-of-function detection of pigmentation genes. MNT-1 cells were transfected with siRNAs targeting tyrosinase using a microtiter-plate based high throughput reverse transfection protocol (Whitehurst et al. 2007) optimized for this cell line. Inhibition of pigmentation and tyrosinase expression relative to control non-targeting siRNAs is shown. b, MNT-1 pigmented melanoma cells were transfected with 84,920 siRNA duplexes targeting 21,230 genes in a one-well, one-gene reverse transfection format as we have previously described (Whitehurst et al. 2007). 120 hrs post transfection, Raw $A_{405\ nm}$ absorbance values were collected for each well and normalized to internal reference samples on each plate, followed by normalization to the experimental mean for each well calculated from the full data set to control for variations in pigment due to plate and position effects. Similarly adjusted luminescence values from a multiplexed viability assay (Cell Titer Glo) were used to control for cell number, generating "normalized absorbance ratios" for each well (absorbance/cell number; Table 1). The log 2 transformation of the average normalized absorbance ratios among replicates is shown for each gene from lowest (hypopigmentation) to highest (hyperpigmentation). Values below 2 standard deviations from the mean are shown in red.

Studies to determine the key molecular regulators of melanogenesis in human melanocytes have been hampered by the innate fragility of these cells and the fact that they produce scant amounts of pigment in culture (Smit et al. 1997; Smit et al. 1998). To identify novel regulators of melanogenesis in human cells, we utilized MNT-1 melanoma cells to screen a genome-wide synthetic siRNA library for single-gene loci that support melanocyte pigmentation. MNT-1 cells produce substantial amounts of melanin in culture, have a gene expression profile that is most similar to normal melanocytes (Hoek et al. 2004), and have been used by others to identify pigment regulatory mechanisms that govern normal melanogenesis (Kushimoto et al. 2001; Theos et al. 2005; Di Pietro et al. 2006; Theos et al. 2006). We employed a previously described (Whitehurst et al. 2007) library of 84,508 siRNAs corresponding to four unique siRNA duplexes, targeting each of the 21,127 unique human genes arrayed in a one-gene/one-well format on 96 well microtiter plates. A spectrophotometric melanin quantitation assay was coupled with an ATP-dependent luminescence cell viability assay (Cell Titer Glo) to identify siRNAs that decrease melanin production without impacting cell survival. Using tyrosinase depletion as a positive control, we determined that a 5-day posttransfection incubation period was optimal for quantitative detection of impaired melanin production (FIG. 4). Other studies demonstrated that the cell titer glo assay did not interfere with the spectrophotometric quantitation of melanin (data not shown).

Figure 4B:
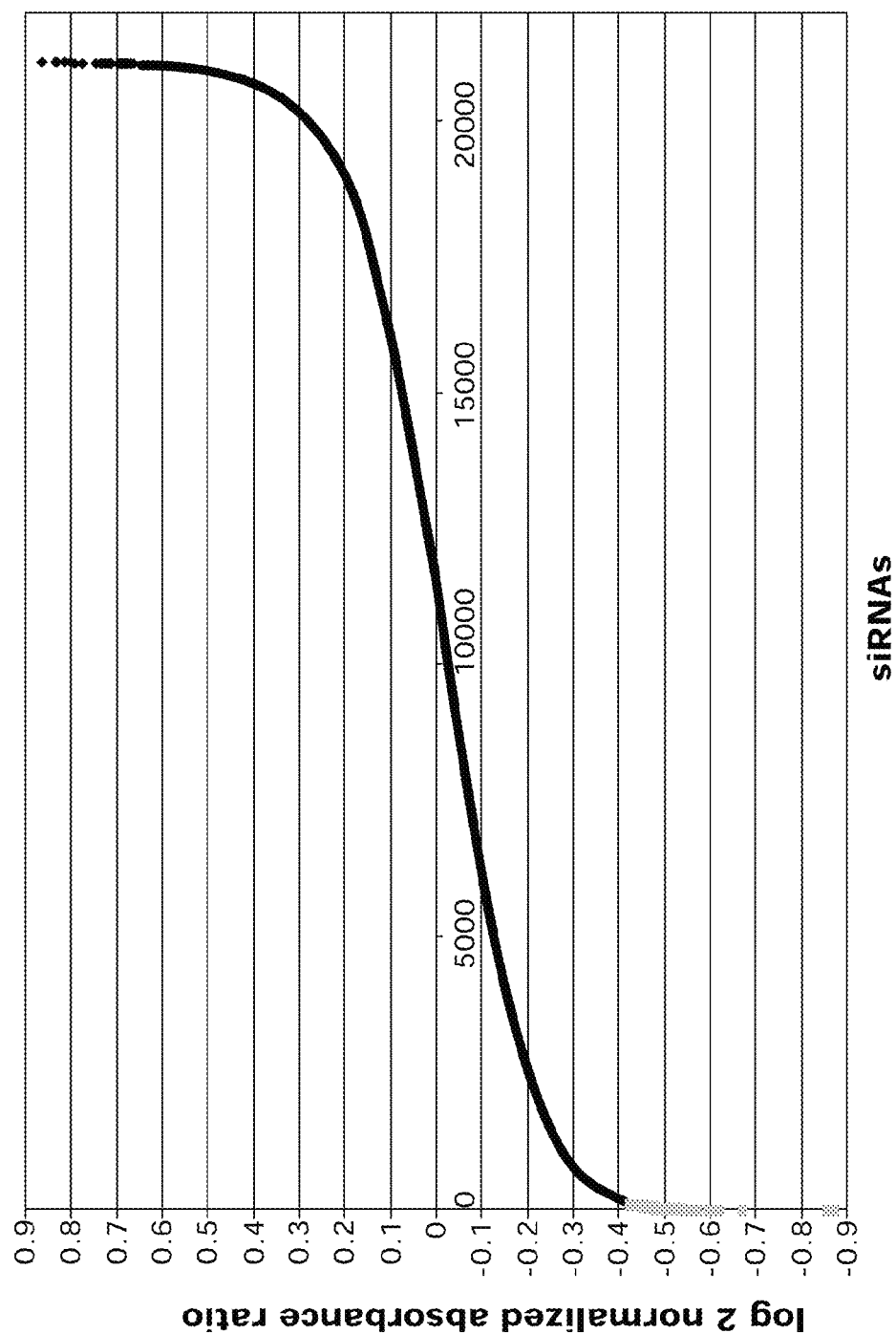

Raw $A_{405\ nm}$ absorbance values were normalized to internal reference samples on each plate to permit plate-to-plate comparisons. This analysis was followed by normalization to the experimental mean for each well location calculated from the full data set in order to control for variations in pigment due to plate position effects. Similarly adjusted luminescence values from the multiplexed viability assay were used to generate "normalized absorbance ratios" for each well. The distribution of the means of these values from duplicate analyses is shown in FIG. 4b. Initial examination of the dataset identified a panel of 13 landmark genes that impaired melanin accumulation when depleted in these assays, with tyrosinase itself scoring with one of the lowest ratios (2.5 standard deviations below the mean; Table 1).

TABLE 1

| Gene Symbol | Accession # | Normalized Percent Inhibition | % error |
|---|---|---|---|
| TYR | NM_000372 | 100 | 3.72 |
| BMP1 | NM_001199 | 84.91 | 1.64 |
| HPS1 | NM_000195 | 77.13 | 1.74 |
| GNA11 | NM_002067 | 75.15 | 3.65 |
| TYRP1 | NM_000550 | 71.19 | 0.65 |
| OCA2 | NM_000275 | 54.57 | 8.04 |
| ATP7A | NM_000052 | 51.68 | 0.84 |
| HPS6 | NM_024747 | 50.91 | 5.52 |
| MUTED | NM_201280 | 48.17 | 2.61 |
| SFXN1 | NM_022754 | 46.95 | 5.44 |
| EDNRB | NM_000115 | 43.29 | 3.96 |
| HPS3 | NM_032383 | 40.85 | 1.15 |
| ZIC2 | NM_007129 | 38.87 | 3.21 |

To facilitate the identification of novel genes that significantly impact melanogenesis, a cutoff of 2 standard deviations below the mean was used to select a candidate hit list (Table 1).

TABLE 2

| | Candidate Pigmentation Genes | | |
|---|---|---|---|
| CATEGORY | SYMBOL | COMMENTS | MOTIFS |
| Autophagy | MAP1LC3C | | MAP1_LC3 |
| | WIPI1 | Expressed in melanoma cell autophagosomes | WD40 |
| | GPSM1 | | GoLoco |
| GPCR | GNG2 | | GGL |
| | GPR113 | | GPS, 7tm_2 |
| | EDNRA | Linked to migraine resistance | 7tm_1 |
| | OR4F15 | | 7tm_1 |
| | EDG7 | | 7tm_1 |
| | GPR92 | | 7tm_1 |
| | AGTR2 | Linked to mental retardation | 7tm_1 |
| | GRM7 | | ANF_receptor, NCD3G, 7tm_3 |
| | GPR84 | | 7tm_1 |
| | P2RY1 | | 7tm_1 |
| Transcription | PLAGL1 | Mutation causes Beckwith-Wiedeman syndrome | Znf_C2H2 |
| | EZH1 | | SANT, SET |
| | TEF | Maps to pigment mutations in mice | BRLZ |
| | GATAD2A | | |
| | ILF2 | | DZF |
| | SMARCC2 | | CHROMO, SWIRM, SANT |
| Pigment | TYR | Albinism | Tyrosinase |
| | BMP1 | | ZnMc, CUB, EGF_CA |
| Phospholipid Signaling | PNPLA4 | | Patatin |
| | ZFYVE1 | | FYVE |
| | ITPK1 | Maps near SNPs linked to pigmentation | L_ns134_P3_kin |
| | PLCXD1 | | PLCc |
| | NRGN | | IQ |
| | PLEKHA1 | Linked to age related macular degeneration | PH |
| Ras Family GTPase | RAB4A | | RAB |
| | HRASLS | | NC |
| | ARL4A | | ARF, small_GTPase |
| | ZDHHC9 | Linked to mental retardation | Zf-DHHC |
| | C5ORF5 | | RhoGAP |
| | ARHGEF11 | | PDZ, RGS, PH, RhoGEF |
| | KLC4 | | Rab5-bind, TPR |
| Protease inhibitor | SERPINB2 | | SERPIN |
| | WFDC8 | | WAP, KU |
| | SERPINE1 | | SERPIN |
| | SERPINB1 | | SERPIN |
| Metabolism | NT5E | | Metallophos, 5_necleotid_C |
| | G6PC3 | | AcidPPC |
| | UROD | Mutation causes porphyria cutanea tarda | URO-D |
| | HPD | Mutation causes tryosinemia type III | Glyoxalase |
| | ALDH9A1 | | Aldedh |
| | PLTP | | BPI1, BP12 |
| | MSRA | Downregulated in vitiligo (hypopigmentation) | PMSR |
| | SMOX | | Amino_oxidase, DAO |
| | UEVLD | | UBC, Ldh_1_N, Ldh_1_C |
| | GMPPB | | NTP transferase, Hexapep |
| | ALDH1A1 | Expression lost in Parkinson's disease | Aldedh |
| | MGC4172 | | Adh_short, Epimerase, KR |
| | ENO2 | | Enolase_N, Enolase_C |
| Protein Phosphorylation | NLK | | S_TKc |
| | PKN2 | | Hr1, C2, S_TKc, S_TK_X |
| | RIOK1 | | RIO |
| | PPP1R15A | Expression lost in melanoma transformation | |
| | PPP2CB | | PP2Ac |
| Helicase | RTEL1 | | DEXDc, HELICc |
| | LOC389901 | | Ku, SAP DNA bd |

TABLE 2-continued

Candidate Pigmentation Genes

| CATEGORY | SYMBOL | COMMENTS | MOTIFS |
|---|---|---|---|
| Peptidase | ARTS-1 | | Peptidase_M1 |
| | KLK13 | | Tyrp SPc |
| | LYZ | Amyloidosis | LYZ1 |
| | ADAM19 | | Pep_M12B_propep, Reprolysin, DISIN, ACR, EGF_2 |
| | CPZ | | FRI, Zn_pept |
| | TRY1 | | Tryp_SPc |
| | SENP1 | | DSS1_SEM1 |
| | SHFM1 | Split hand/foot malformation | Peptdiase_C48 |
| Translation | EEF1A1 | | GTP_EFTU, GTP_EFTU_D2, GTP_EFTU_D3 |
| | VARS2 | | tRNA-synt_1, Anticodon_1 |
| other | NPM3 | | Nucleoplasmin |
| | STX18 | | Syntaxin |
| | KRTAP4-11 | | Keratin_B2 |
| | FGF23 | Overexpressed in hyperpigmentation syndrome | FGF |
| | SFRS2 | | RRM |
| | SLC17A5 | Mutation causes Salla disease | MFS_1 |
| Unknown | USHBP1 | | |
| | UBE2V1 | | UBCc |
| | TEX1 | | TPR_2 |
| | TANC2 | | ANK, TPR |
| | FATE1 | | |
| | LRRC1 | | LRR |
| | RTN3 | | Reticulon |
| | SPATA22 | | |
| | ETAA1 | Tumor antigen, melanoma of soft parts | |
| | c12orf49 | | |
| | FAM125B | | |
| | HSPC049 | | WD40 |
| | AFAP1L2 | | PH |
| | FLJ41423 | | |
| | MAGEA6 | Melanoma antigen | MAGE |
| | MUC3b | | EGF, SEA |
| | C1orf194 | | NuA4 |
| | FAM89B | | |

Of the 98 genes identified in the primary screen, only 6/98 genes exhibited aberrant expression in MNT-1 cells as compared to normal melanocytes (Hoek et al. 2004), indicating that the screen identified a large number of genes that likely impacted melanogenesis in both primary melanocytes and MNT-1 cells.

Figure 1C:
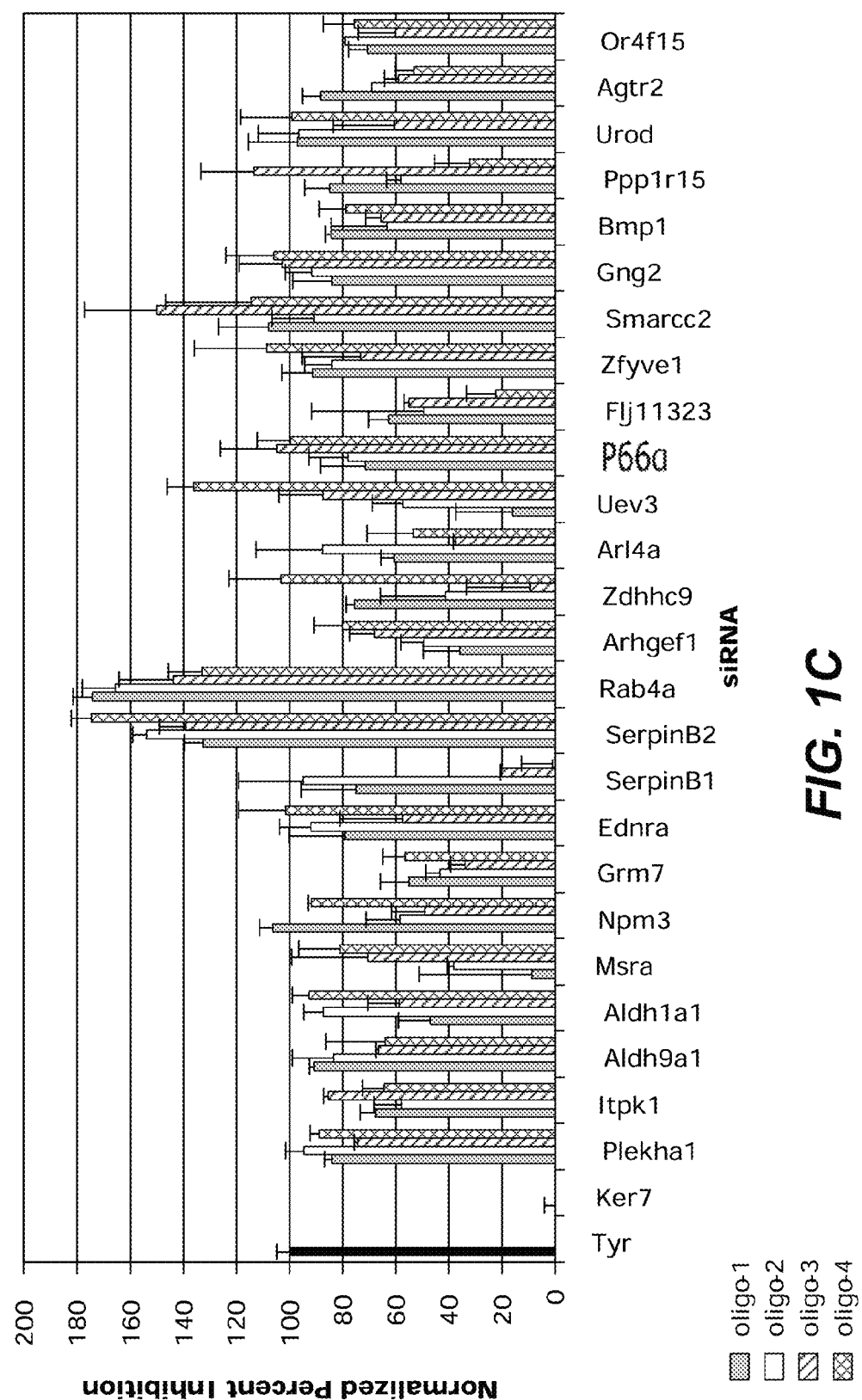
Figure 5A:
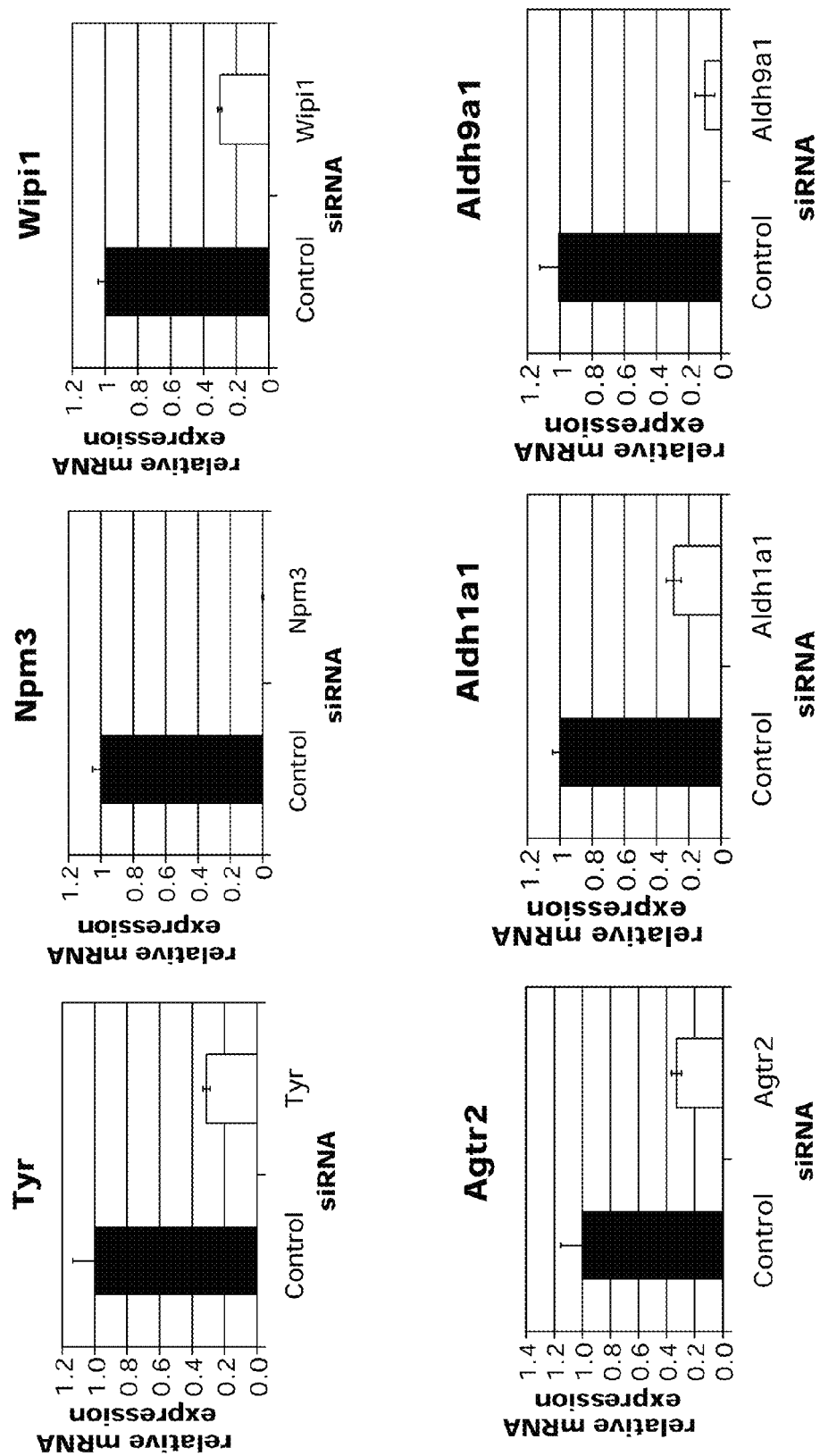
FIG. 5A-B. Quantitative RT-PCR was employed to measure the impact of pooled siRNAs on target mRNA levels. Actin primers were employed to control for mRNA concentrations. Results are representative of three experiments performed in triplicate.
Figure 5B:
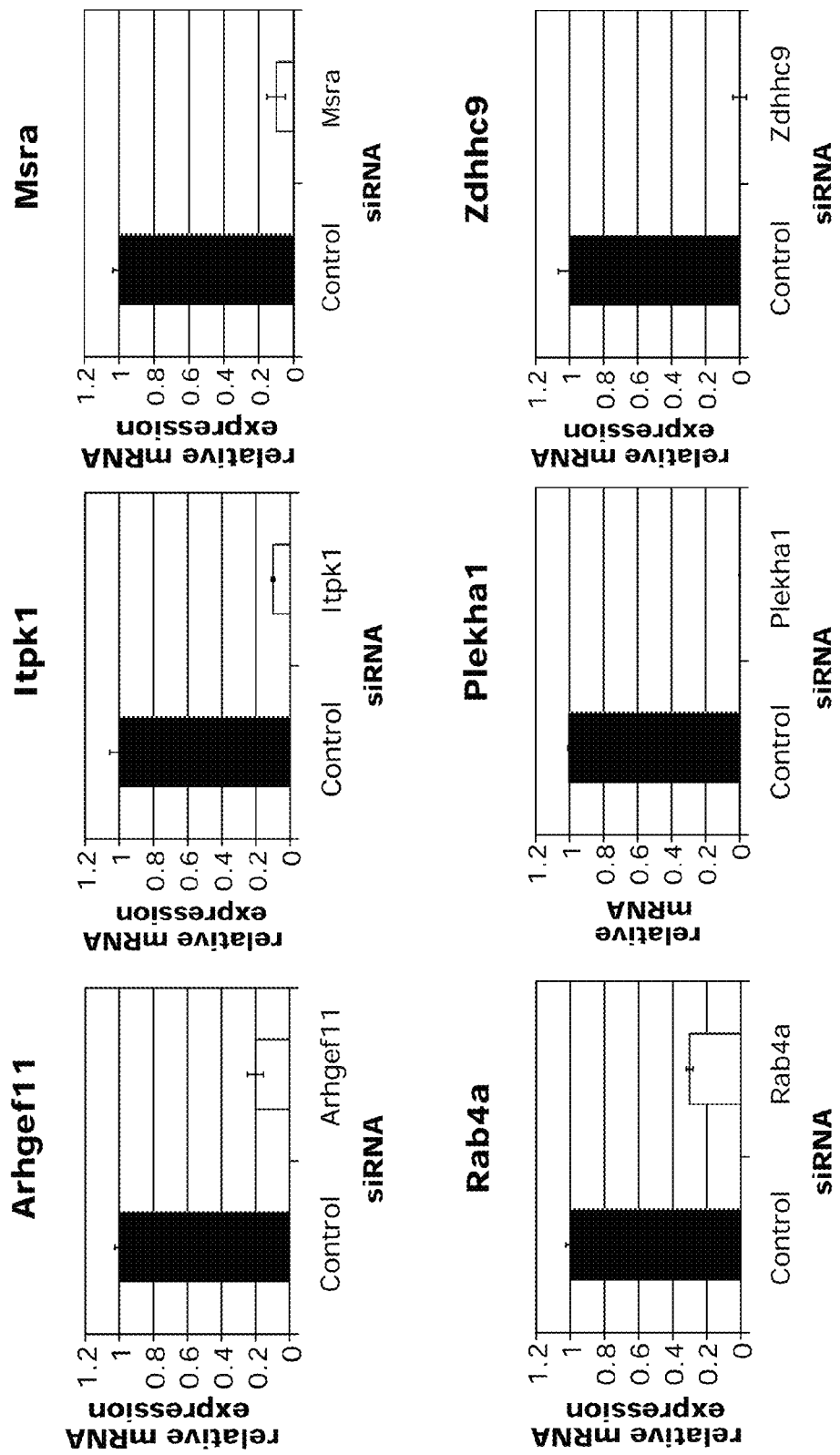

Individually synthesized, pooled siRNAs directed against 33 of the 98 genes selected from the primary screen, as described above, were retested to determine the false-positive rate. To more precisely control for the efficacy of siRNA transfection and to correct for the background absorbance of MNT-1 cells, the ability of each target siRNA to inhibit pigment production was compared to the ability of tyrosinase siRNA to inhibit pigment production using a normalized percent inhibition calculation (Malo et al. 2006), and relative pigmentation was assessed visually prior to cell lysis (FIGS. 1a,b). A Keratin 7 siRNA pool that did not impact pigment production was utilized as a negative control. Four siRNA pools failed to significantly impact pigment production upon retesting and were eliminated from further analysis (FIG. 1a, Table 3), giving an estimated false discovery rate of 12.1%. Quantitative RT PCR indicated that each siRNA pool inhibited the expression of the appropriate target gene (FIG. 5). To eliminate siRNA pools with off-target effects on melanogenesis (Whitehurst et al. 2007), the four siRNAs comprising each siRNA pool were retested individually. We found that at least two independent siRNAs against each target gene significantly inhibited pigment production (FIG. 1C, Table 3), suggesting that pigmentation phenotypes are not a common consequence of siRNA off-target phenomena. Together, these studies demonstrate that the genome wide siRNA screening platform accurately identified gene targets that specifically impact pigment production.

TABLE 3

| siRNA | Pool | Oligo 1 | Oligo 2 | Oligo 3 | Oligo 4 |
|---|---|---|---|---|---|
| Tyr | 3.00E−06 | 1.01E−04 | 3.37E−04 | 2.15E−04 | 4.14E−04 |
| Plekha1 | 6.24E−03 | 8.69E−05 | 1.69E−04 | 1.22E−04 | 7.67E−05 |
| Itpk1 | 1.30E−03 | 2.48E−03 | 2.86E−03 | 9.30E−04 | 3.55E−03 |
| Aldh9a1 | 1.87E−02 | 3.24E−03 | 5.46E−03 | 1.17E−02 | 4.48E−02 |
| Aldh1a1 | 1.98E−02 | 6.95E−02 | 5.41E−03 | 2.53E−02 | 3.39E−03 |
| Msra | 4.63E−03 | 7.97E−01 | 4.46E−02 | 4.60E−02 | 5.85E−03 |
| Npm3 | 5.83E−03 | 5.16E−05 | 8.58E−04 | 5.13E−03 | 5.39E−05 |
| Grm7 | 8.90E−04 | 1.56E−03 | 3.35E−04 | 1.77E−02 | 6.96E−04 |
| Ednra | 1.63E−04 | 3.19E−03 | 3.49E−04 | 1.48E−02 | 7.10E−04 |
| SerpinB1 | 2.47E−04 | 3.68E−03 | 2.66E−05 | 3.40E−03 | 9.04E−01 |
| SerpinB2 | 5.43E−03 | 2.10E−04 | 1.93E−04 | 2.27E−04 | 7.69E−05 |
| Rab4a | 4.34E−03 | 7.45E−05 | 6.12E−04 | 6.95E−04 | 3.70E−04 |
| Arhgef11 | 4.45E−04 | 1.36E−02 | 3.78E−04 | 4.32E−04 | 3.21E−04 |
| Zdhhc9 | 1.66E−03 | 3.66E−05 | 6.59E−03 | 5.38E−01 | 9.17E−04 |
| Arl4a | 2.54E−02 | 1.45E−02 | 4.57E−03 | 5.99E−02 | 3.76E−02 |
| Uev3 | 1.54E−02 | 2.76E−01 | 1.73E−02 | 1.09E−03 | 3.70E−05 |
| P66alpha | 1.19E−02 | 2.50E−03 | 6.42E−03 | 1.19E−03 | 2.61E−04 |
| Flj11323 | 2.51E−02 | 1.39E−02 | 3.56E−02 | 1.88E−02 | 2.26E−01 |
| Zfyve | 8.97E−03 | 3.02E−04 | 6.89E−02 | 5.19E−03 | 2.56E−03 |
| Smarcc2 | 1.63E−03 | 1.36E−03 | 2.47E−02 | 1.12E−03 | 4.97E−03 |
| Gng2 | 3.75E−03 | 7.95E−04 | 1.92E−04 | 5.21E−04 | 6.60E−04 |

TABLE 3-continued

| siRNA | Pool | Oligo 1 | Oligo 2 | Oligo 3 | Oligo 4 |
|---|---|---|---|---|---|
| Bmp1 | 1.22E-03 | 1.66E-05 | 2.85E-03 | 1.29E-04 | 2.93E-04 |
| Ppp1r15a | 9.48E-04 | 2.02E-04 | 1.05E-03 | 7.13E-04 | 1.83E-02 |
| UroD | 3.34E-03 | 1.03E-03 | 1.69E-02 | 1.21E-02 | 1.09E-03 |
| Agtr2 | 1.71E-03 | 1.42E-04 | 2.94E-04 | 5.36E-04 | 1.14E-03 |
| Or4f15 | 1.48E-02 | 2.05E-04 | 1.13E-03 | 2.45E-03 | 6.07E-04 |
| Wipi1 | 9.10E-04 | 8.31E-05 | 1.93E-05 | 3.41E-04 | 1.39E-05 |
| gpsm1 | 3.91E-05 | 1.59E-05 | 1.04E-04 | 4.34E-04 | 5.22E-06 |
| map1lc3a | 4.76E-03 | 2.94E-05 | 5.35E-04 | 7.84E-05 | 1.02E-04 |
| map1lc3c | 9.98E-03 | 4.59E-05 | 1.57E-04 | 2.33E-05 | 3.77E-05 |
| Becn1 | 1.67E-03 | 3.02E-07 | 7.39E-05 | 2.13E-06 | 2.81E-07 |
| Rps6ka3 | 3.66E-01 | n/a | n/a | n/a | n/a |
| AldoB | 7.60E-02 | n/a | n/a | n/a | n/a |
| Acox3 | 1.10E-01 | n/a | n/a | n/a | n/a |
| Gpr113 | 1.92E-01 | n/a | n/a | n/a | n/a |

Figure 2A:
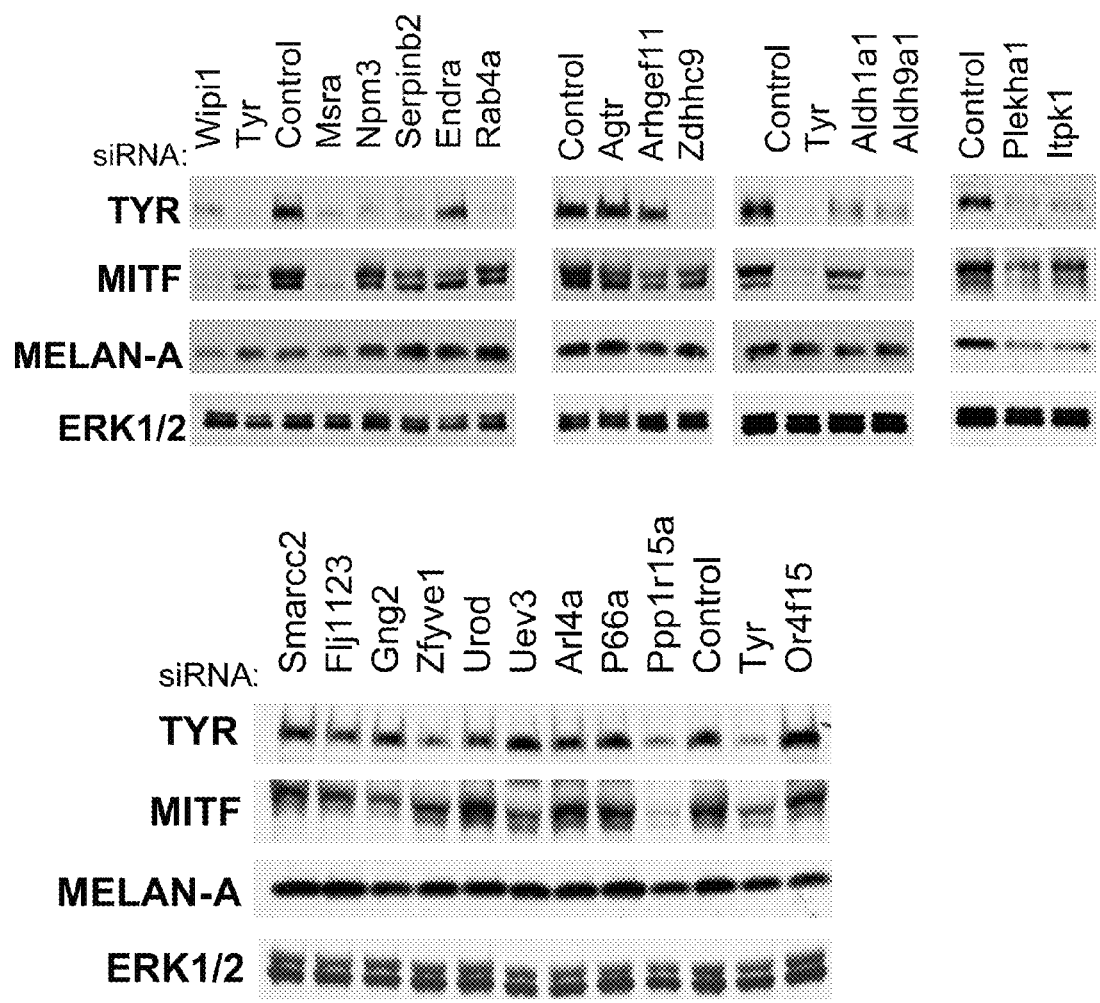
FIG. 2A-G. Novel, pharmaceutically-tractable melanogenesis gene networks converge on tyrosinase expression. a, 4 days post transfection with the indicated siRNAs, MNT-1 whole cell lysates were prepared and analyzed by immunoblot for the indicated proteins. A non-targeting siRNA was used as a transfection control (Control). ERK1/2 is shown as a loading control. b, Those siRNAs that inhibited tryosinase accumulation were examined for consequences on Tyrosinase and MITF gene expression by quantitative rt-PCR. c, The indicated siRNAs, targeting novel pigmentation genes identified in the MNT-1 screen, were tested for consequences on tyrosinase protein accumulation in darkly pigmented primary human melanocyte cultures 6 days post transfection as in a. d, The indicated siRNAs, targeting novel pigmentation genes identified in the MNT-1 screen, were tested for consequences on tyrosinase protein accumulation in moderately pigmented primary human melanocyte cultures 6 days post transfection as in a. e, Pharmacological inhibition of Aldh activity impacts tyrosinase protein accumulation. MNT-1 cells (left panel) and primary melanomcyte cultures (right panels) were exposed to 5 uM Aldh inhibitors (cyanamide or Angeli's salt) or the tyrosinase inhibitor hydroxyquinone(Kim and Uyama 2005) for 72 hours as indicated. 24 hours post treatment, cultures were exposed to UV-B at the doses indicated. Tyrosinase and ERK1/2 levels were assessed by immunoblot. MNT-1: Angeli's salt (5 uM), cyanamide (5 uM), or hydroquinone (5 uM); primary melanocytes: Angeli's salt (50 uM), cyanamide (100 uM), hydroquinone (1 uM). f, Aldh inhibitors impair melanogenesis in primary human melanocytes. Darkly pigmented melanocytes were cultured for seven days in the presence of the indicated dosed of cyanamide, vehicle, or PTU. PTU is the most potent currently known in vitro pigment inhibitor in primary melanocytes(Hall and Orlow 2005). Subsequently, cells were lysed in Cell Titer Glo and the luminescence and absorbance values were used to calculate inhibition of pigmentation as in FIG. 1a. g, MNT-1 cells transfected with the indicated siRNAs as in a were incubated in the presence and absence of bafilomycin A2 for 24 hours prior to lyses and analyses of tyrosinase protein accumulation. All results shown are representative of a minimum of three independent experiments.
Figure 2B:
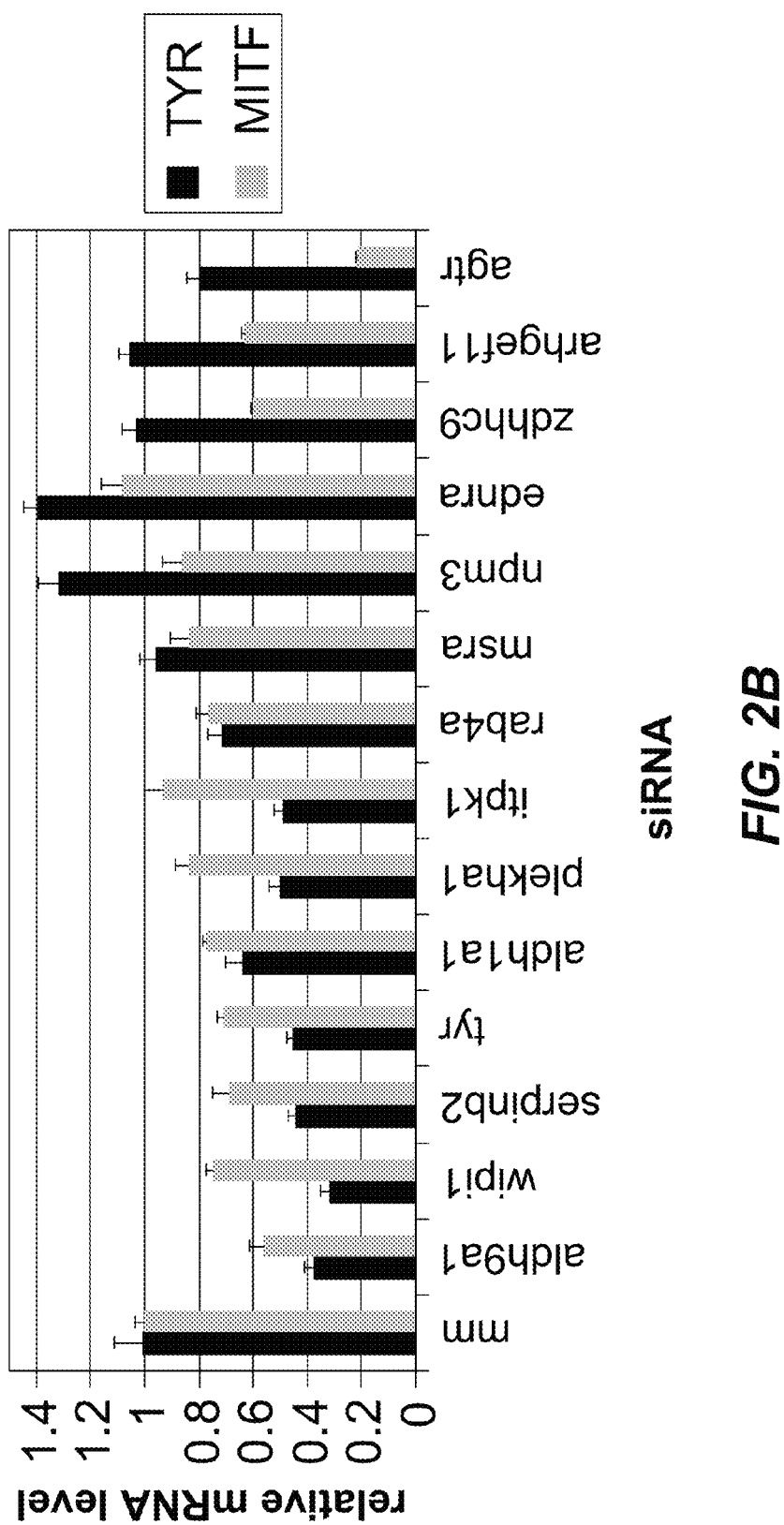
Figure 6:
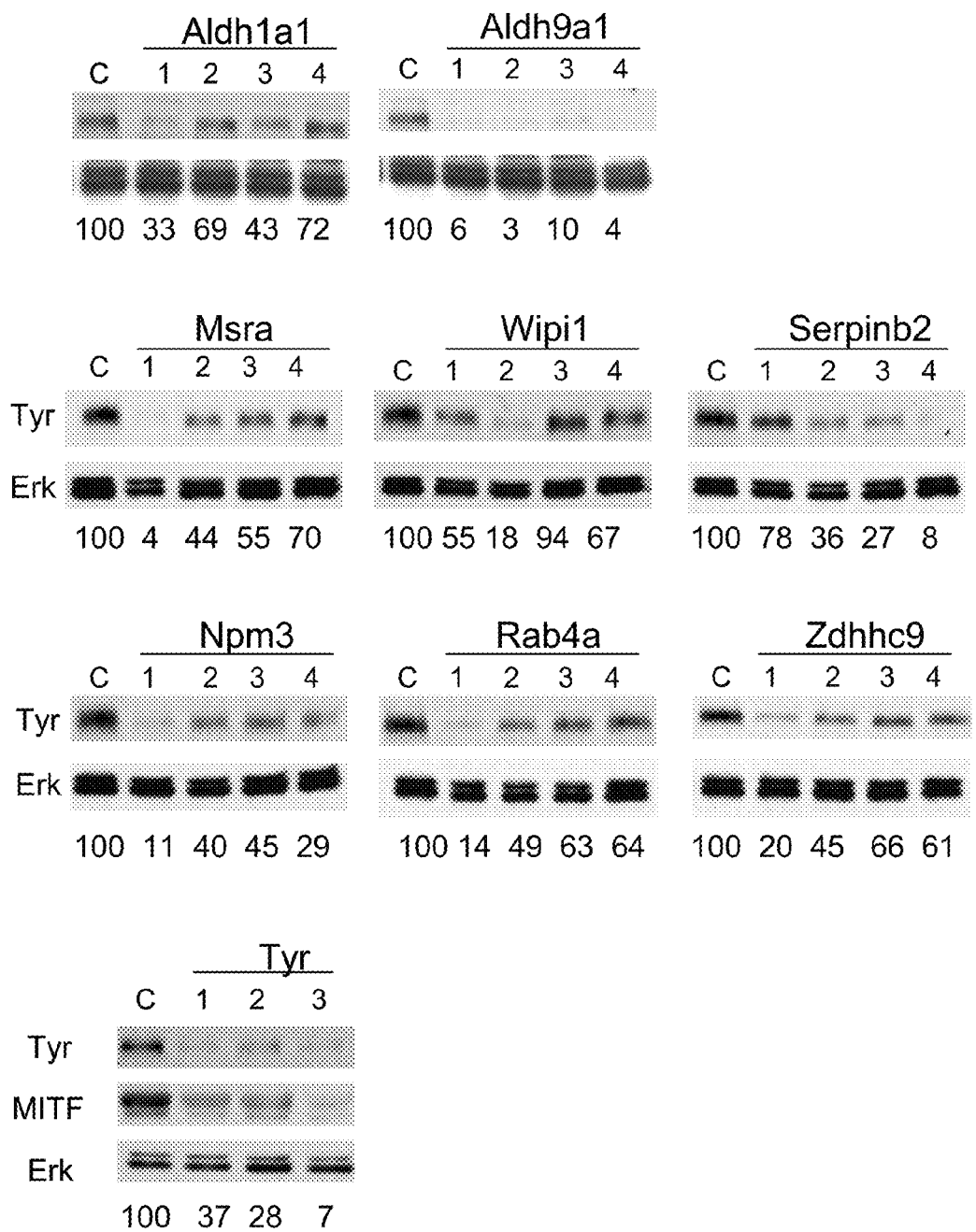
FIG. 6. The impact of multiple independent siRNAs, targeting the indicated genes, on tyrosinase protein accumulation was assessed by immunoblot. Two or more siRNAs significantly impaired tyrosinase protein expression in all cases examined. Similarly, the impact of multiple independent siRNAs targeting tyrosinase on MITF protein accumulation was assessed by immunoblot. All three siRNAs tested had an impact on MITF expression.
Figure 7:
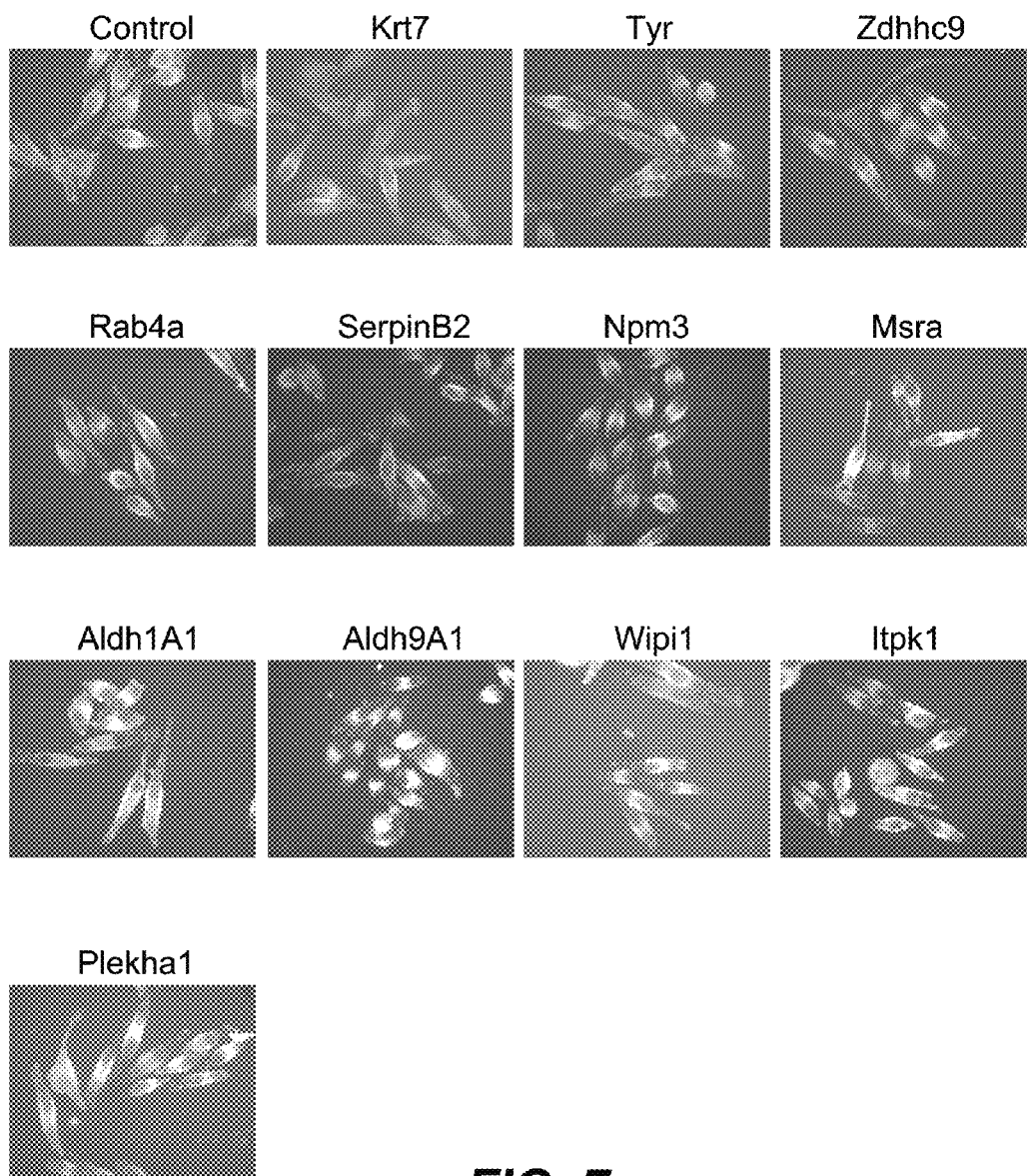
FIG. 7. MNT-1 cells transfected with the indicated siRNAs were immunostained with anti-Pmel antibodies to detect melanosomes 4 days post transfection. Representative micrographs are shown.

Initial examination of existing gene ontology data for our pigment regulators exposed a wide variety of cellular processes represented by the validated and candidate hits (Table 2). Therefore, we employed a focused unbiased approach to identify regulators of tyrosinase, the rate limiting enzyme specifying melanogenesis (Kim and Uyama 2005) among novel validated genes supporting MNT-1 pigmentation. Relative accumulation of tyrosinase, the melanogenesis transcription factor MITF, and the melanosomal marker protein Melan-A were examined 96 hours post siRNA transfection. Remarkably, over half of the validated pigment genes appear to be required for tyrosinase protein accumulation (FIG. 2A, FIG. 6). This defect did not appear to be a gross inhibition of cell fate specification, as Melan-A expression was mostly unaffected. In addition, the subcellular morphology of PMEL17, a melanosome structural protein (Kobayashi et al. 1994), was normal at the level of immunofluorescence detection (FIG. 7). Of those pigment genes impacting tyrosinase accumulation, approximately half appear to act at the level of transcription (FIG. 2B), and several of these also impaired MITF expression. Given that tyrosinase is an MITF target gene, the pigmentation genes in this later class may represent action at the level of MITF expression. A caveat to this interpretation is our observation that siRNA-mediated turnover of tyrosinase mRNA can also lead to inhibition of MITF gene expression (FIG. 2A) through a relationship that remains to be defined. Preliminary studies indicated that this phenotype was not a consequence of siRNA off-target phenomenon (FIG. 6).

Figures 2C, 2D:
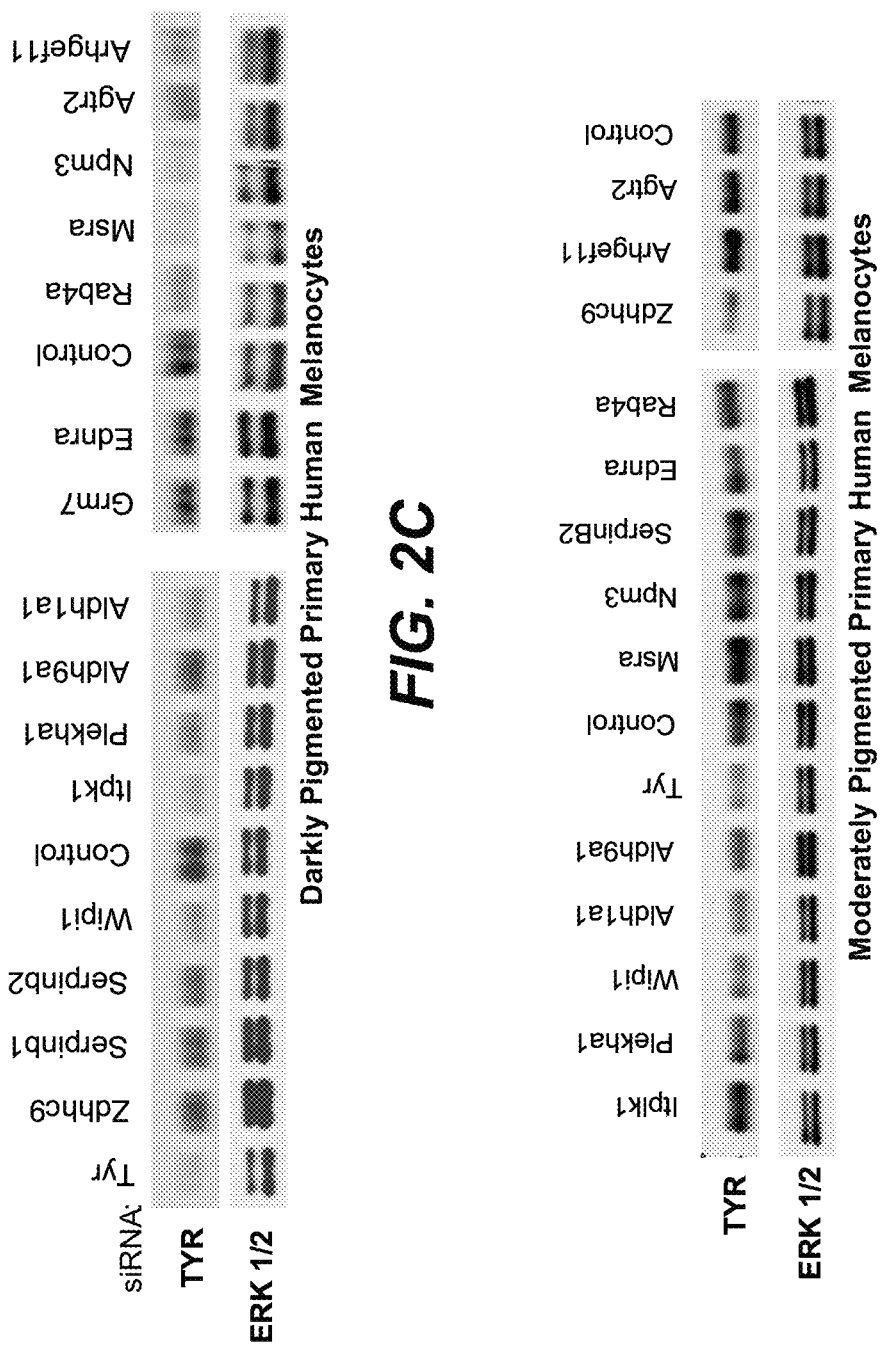

While pigmentation in humans is a complex multigenic trait, the degree of genetic variation that contributes to melanocyte autonomous pigment production is unknown. To examine the phenotypic penetrance of novel pigmentation genes, identified in MNT-1 cells, in diverse genetic backgrounds, we employed primary human melanocyte cultures isolated from two different individuals. Remarkably, the majority of targets that regulated tyrosinase expression in MNT-1 cells also impacted tyrosinase expression when depleted from darkly pigmented primary melanocytes (FIG. 2C). Approximately half of these targets also inhibited tyrosinase expression when depleted from moderately pigmented melanocytes (FIG. 2D). These results indicate that the primary screen returned numerous previously unappreciated core components of pigment production machinery. Selective activity of some targets in different genetic backgrounds is reminiscent of pigmentation as a complex genetic trait, and may reflect molecular components that drive phenotypic variation.

Figure 2E:
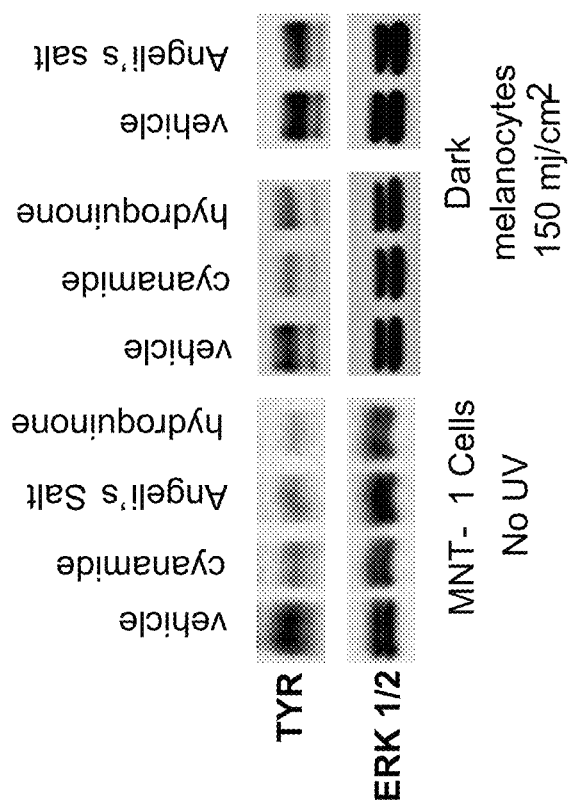
Figure 2F:
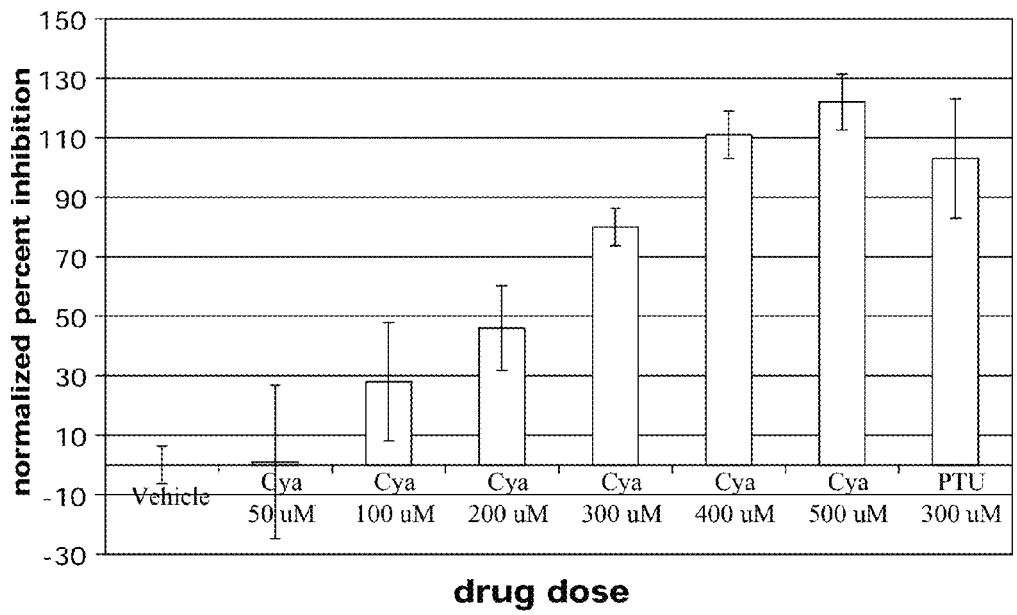

For further analyses, we focused on those novel pigmentation genes that impacted tyrosinase expression in all three genetic backgrounds. Among these were two isoforms of aldehyde dehydrogenase, Aldh1 and Aldh9, well characterized enzymes that regulate ethanol detoxification (Edenberg 2007). A number of chemical inhibitors of these enzymes have been identified (DeMaster et al. 1998), and several of these agents are clinically utilized to induce alcohol intolerance during detoxification interventions; presenting an opportunity for pharmacological validation of the contribution of Aldh activity to melanocyte pigmentation. Disulfiram is an Aldh inhibitor that is toxic to melanoma cells via a mechanism that is independent of Aldh inhibition (Cen et al. 2002). However, two non-toxic Aldh inhibitors, cyanamide and Angeli's salt (DeMaster et al. 1998), inhibited pigmentation and tyrosinase protein accumulation in MNT-1 cells at doses that are equivalent to those required for inhibition of Aldh activity in culture (FIG. 2E). In addition, these compounds impaired UV-induced tyrosinase expression when tested in primary melanocytes (FIGS. 2E,F).

The identification of Plekha1 as a gene product that supports melanogenesis is significant due to the tight linkage of polymorphisms at this locus to age related macular degeneration (ARM), a disorder that can be a consequence of decreased melanin deposition in the retinal pigment epithelium. Plekha1 is a PtdIns(3,4)P(2)-binding protein that has been suggested to modulate phosphoinositide-3-kinase-dependent signaling by recruitment of phosphatase activity for feedback inhibition. Its identification in this screen indicates a causal relationship between Plekha1 function and susceptibility to ARM. Importantly, Plekha1 homozygous null mice exhibit skin pigmentation defects, microopthalmia, and increased intrapupillary distance; phenotypes that are similar to those observed in MITF haploinsufficient animals (J. Schmahl and P. Soriano, personal communication).

Figure 2G:
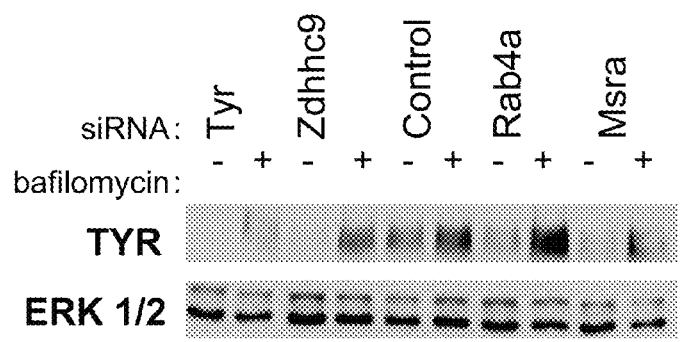

Melanosomes are distinct lysosome-related organelles dependent upon appropriate post-golgi sorting events for delivery of functionalizing "cargo" including tyrosinase (Raposo et al. 2007). Therefore, impaired accumulation of tyrosinase can be a consequence of missorting to lysosomes and subsequent hydrolyses in that organelle. To define target genes that may participate in this sorting event, lysosome acidification was inhibited by bafilomycin A exposure subsequent to target gene depletion (Watabe et al. 2004). As shown in FIG. 2G, a 24 hour inhibition of lysosome acidification rescued tyrosinase accumulation upon depletion of the small G-protein Rab4a, and the small G-protein palmitoyltransferase Zdhhc9. By contrast, bafilomycin did not restore tyrosinase accumulation upon depletion of Msra, a protein that can protect against oxidative damage through reduction of methionine sulfoxide.

Figure 3A:
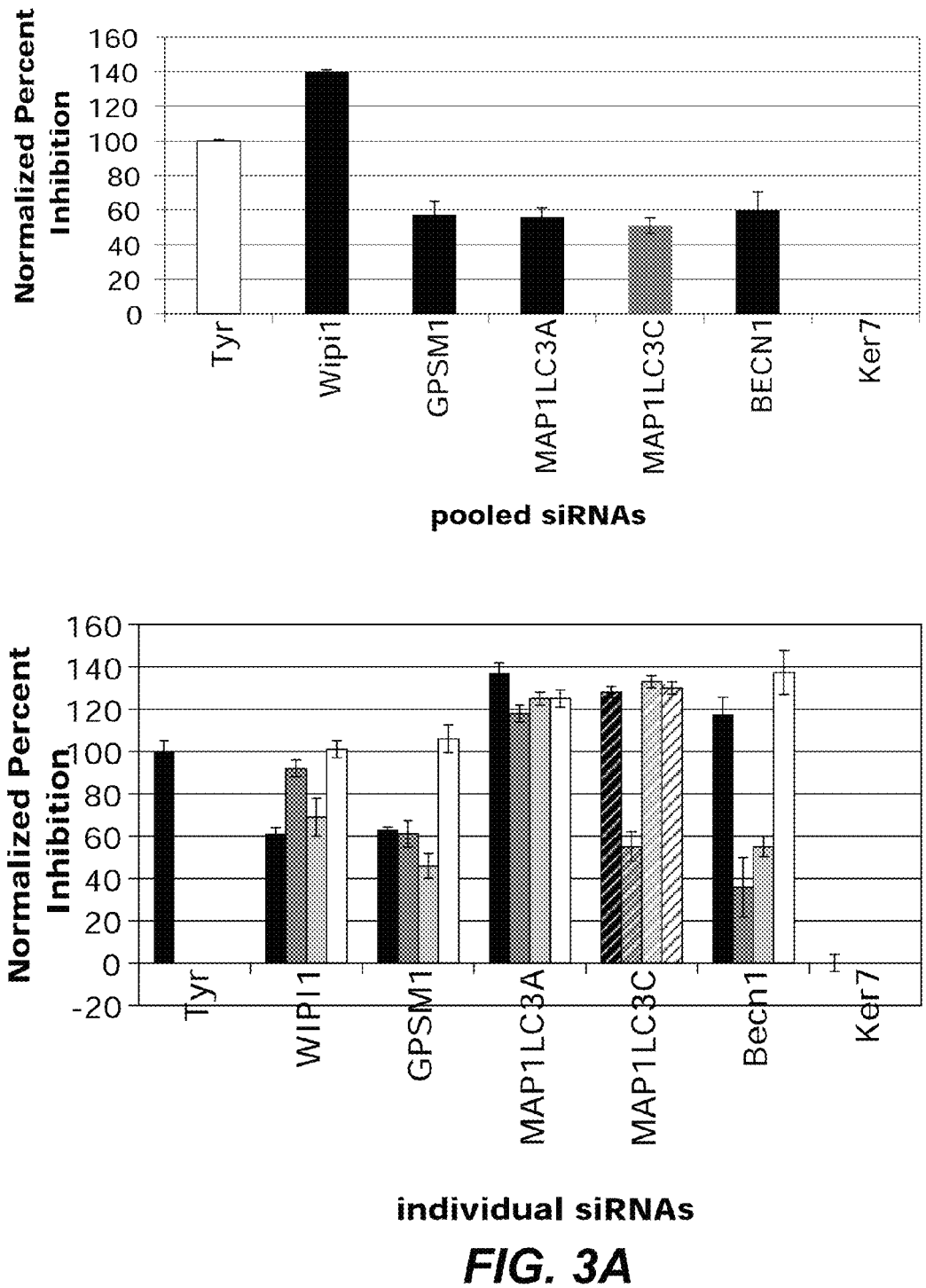
FIG. 3A-D. Autophagy is a novel biological process regulating melanin formation. a, MNT-1 cells were transfected with the indicated siRNA pools (50 nM final concentration) or individual siRNAs (75 nM final concentration) targeting putative genes that regulate autophagy identified in the primary screen as described in FIG. 1. Bars represent mean and s.e.m. for n=3. b, Coat color defects in autophagy impaired mice. The coat pigmentation of C57B6 wild type (+/+) and heterozygous beclin 1 mutant littermates (+/−) is shown. c, Reduced melanin accumulation in the hair follicles of Beclin1 haploinsufficient mice. Skin samples from beclin 1 haploinsufficient mice and wild type littermates were fixed and sectioned. Upper panels: Fontana-Masson silver staining was used to assess melanin content in the hair follicle (arrow). Detection of staining in wild-type follicles is obscured by accumulation of opaque pigment granules (left panel, and occasional normal follicles in the beclin+/− background (arrow head)). Sections were counter-stained with aqueous neutral red. Lower panels: the melanocyte and neuronal cell marker S100 was used to identify melanocytes in the hair follicle bulb (arrow). Again, staining is obscured in normal follicles due to accumulation of opaque pigment granules. d, MNT-1 cells were fixed and stained with the primary antibodies indicated. Two photon confocal microscopy was utilized to visualize the colocalization of autophagy and melanosome markers. Representative 0.2 M confocal slices are shown.
Figure 3B:
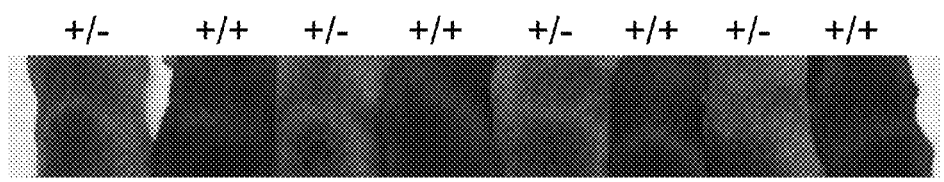
Figure 3C:
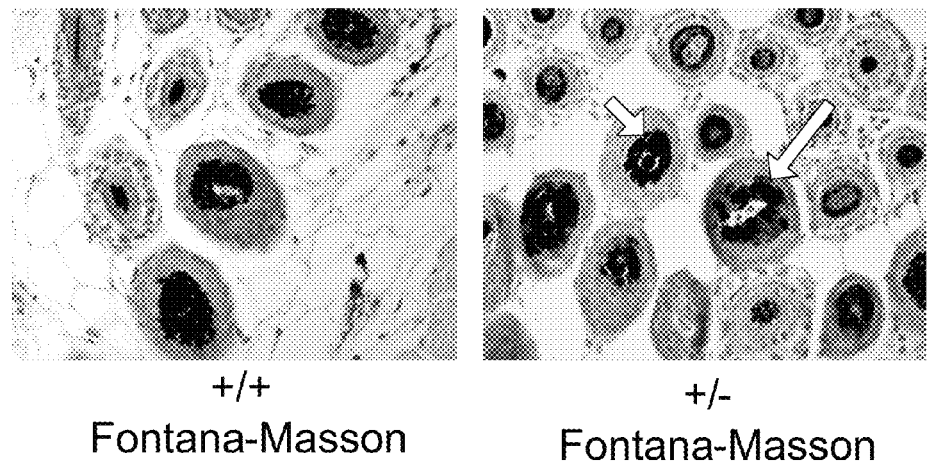
Figure 3C:
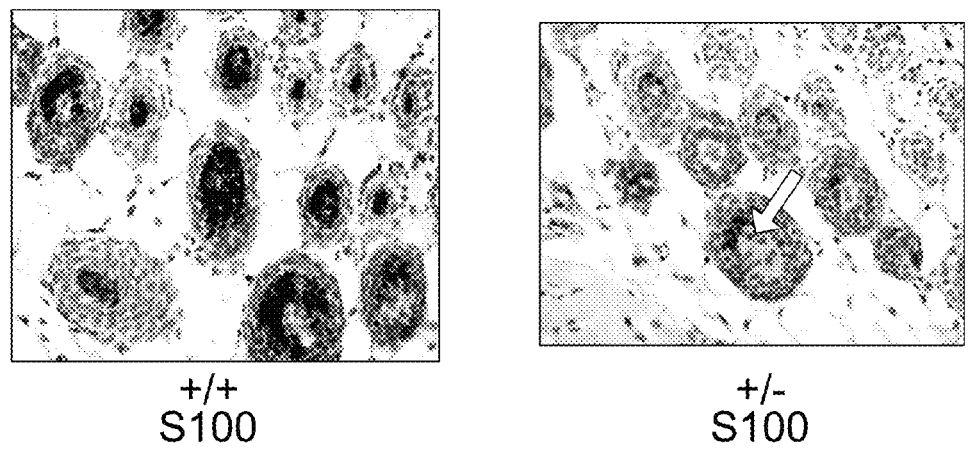
Figure 3D:
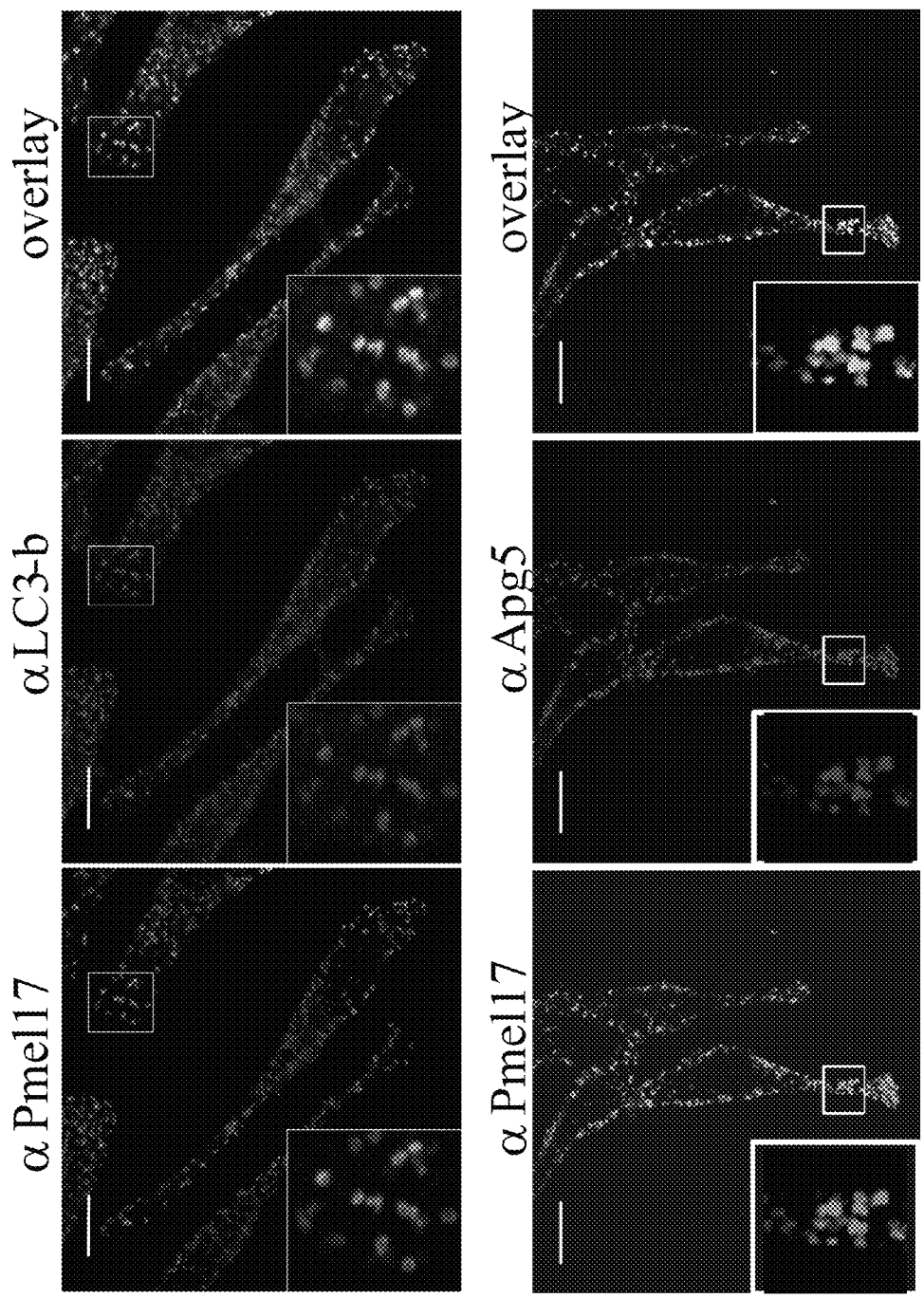

Among the panel of validated pigment regulatory genes with phenotypic penetrance in multiple genetic backgrounds was WIPI1 (FIG. 2). Wipi1 has been implicated as a human homolog of the yeast autophagy protein ATG18, and is localized to starvation-induced autophagosomes in human cell culture (Proikas-Cezanne et al. 2004). Two additional autophagy-related proteins, LC-3c and GPSM1/AGS3 were isolated in the primary screen (Table 2). Validation of these targets by siRNA pool deconvolution suggested a functional relationship between autophagosome and melanosome biogenesis (FIGS. 3a, 3b). Furthermore, we found that depletion of two additional components required to trigger autophagosome formation, BECN1 or LC3-a, severely impaired pigment accumulation (FIG. 3a). Failure to recover these genes in the primary screen is indicative of the false discovery rate inevitably associated with high throughput. Consistent with this relationship, heterozygous deletion of the autophagy protein Beclin 1 (Qu et al. 2003) results in a dramatic coat color defect in mice (FIG. 3B). Homozygous null mutations are embryonic lethal, however haploinsufficient animals show profound inhibition of melanin synthesis and accumulation in the hair follicle despite the presence of melanocytes in the hair follicle bulb and neck regions (FIG. 3C). As melanosomes are thought to be lysosome related organelles, autophagic machinery may be required for the functional sorting of melanin synthetic machinery. At the cell autonomous level, we found acute colocalization of the autophagy protein LC3 and the melanosome markers Pmel17 and Apg5 in mature melanosomes (FIG. 3D). Thus molecular components required for autophagosome formation are directly implicated in the biogenesis of melanin, either at the level of melanosome formation or melanosome maturation.

We have utilized an unbiased, high-throughput functional genomics screening platform to identify critical single gene loci that regulate the nefariously complex, highly regulated process of melanogenesis in human cells. Using this approach, we have identified several novel pigment regulatory mechanisms that impact melanogenesis in the eye, brain, and skin. The convergence of several of these loci directly on the critical rate-limiting enzyme in melanogenesis, tyrosinase, underscores the power of this approach to identify unrecognized regulatory networks that directly impact even well characterized enzymatic pathways. The complexity of the network controlling tyrosinase expression uniquely parallels the variation in skin color seen in human skin, underscored by the fact that these mechanisms are differentially active in moderately and darkly pigmented melanocytes. The direct identification of novel compounds that inhibits melanogenesis highlights the utility of genome wide siRNA screening as a translational approach for deriving novel molecular based treatment strategies in the post genomic era.

These and further related results are described in Ganesan, A. K., et al., PLoS Genetics 4(12) e1000298:1-12, which is hereby incorporated by reference in it's entirety, and in particular for its description of genome-wide siRNA-based functional genomics studies of pigmentation.

Methods

Cell Culture and Reagents.

MNT-1 cells were a gift of M. Marks (University of Pennylvania). These cells were cultured in DMEM (Invitrogen) with 15% fetal bovine serum (hyclone) and 1× antibiotic/antimycotic (invitrogen). Darkly pigmented and moderately pigmented melanocytes were purchased from Cascade biologics. These cells were cultured in Medium 254 with the melanocyte specific HMGS2 supplement (Cascade biologics). Beclin 1 heterozyous mice were obtained from Beth Levine. Angeli's salt was a gift from Pat Farmer. Cyanamide was purchased from Sigma. Bafilomycin was purchased from Tocris biosciences. The genome wide siRNA library used in these studies was previously described (Whitehurst et al.). RPMI 1640 (Invitrogen) was media used for creating lipid oligonucleotide mixtures. All transfections utilized Dharmafect-2 transfection reagent (Dharmacon). Tyrosinase, MITF, Erk, Melan A, Apg5, LC3, Pmel17 and all secondary antibodies for immunoblot analysis were purchased from Santa Cruz Biotechnology. Secondary antibodies for immunofluorescence were purchased from Invitrogen. S100B antibody was purchased from DakoCytomation.

High Throughput Transfection Protocol.

High throughput transfection was performed essentially as described (Whitehurst et al. 2007) with slight modifications. 0.28 pmoles of each siRNA pool in a volume of 30 ul of RPMI was delivered to each of 6 assay plates/master plate using a Biomek FX robotic liquid handler (Beckman Coulter). 0.1 ul of Dharmafect 2 (Dharmacon) in 9.9 ul of RPMI was then delivered to each well using a TiterTek Multidrop. Following a 20-30 minute incubation, $1 \times 10^4$ MNT-1 cells from a trypsin-mediated single-cell suspension were delivered to the siRNA/liposome complexes in a total volume of 200 ul. Plates were incubated for 120 hours at 37° C./5% CO2 after which a Hydra 96 (Robbins-Scientific) was used to removed 100 ul of the medium. 15 ul of Cell-Titer Glo Reagent (CTG) (Promega) was delivered to each well and incubated according to manufacturer protocol. Luminescence and absorbance values for each well was recorded using an Envision Plate Reader (Perkin Elmer). Each transfection was performed in duplicate.

Data Normalization.

Raw luminescence values collected from the high throughput screen were normalized to internal reference control samples (cells with no siRNA in wells A1-A8) on each plate to allow for plate-to-plate comparisons. These values were used to normalize absorbance values for each well in the plate, effectively controlling for the impact of each siRNA on cell viability. To normalize for positional variation in the plates secondary to prolonged culture times in the humidified incubator, each well in the plate was normalized to the mean value from all wells in the same location. Mean and standard deviation for each data point and the mean and standard deviation of the entire distribution was calculated. siRNAs that produced absorbance/cell titer glo ratios two standard deviations below the mean were subjected to further analysis.

Quantitative RT-PCR.

$6 \times 10^3$ MNT-1 cells were transfected in 96 well plates with 50 nM candidate siRNA using 0.2 ul dharmafect 2 reagent. 48 hours after transfection, cDNA was prepared from transfected cells utilizing a Cells to Ct kit (Ambion) per the manufacterer's protocol. Primers targeting each candidate gene, tyrosinase, actin and MITF were purchased from Applied Biosystems. An aliquot of each cDNA reaction was then added to each Taqman master mix reaction along with the appropriate primer per the manufacturer's protocol (Applied Biosystems). A 7900HT Fast Real-Time PCR System (Applied Biosystems) was utilized to determine Ct values. Values were normalized using actin and analyzed using the relative quantification mathematical model (Pfaffl).

Drug Treatment.

$1 \times 10^4$ MNT-1 cells were plated in a 96 well microtiter plate. 24 hours after plating, cells were incubated with either vehicle, hydroquinone Angeli's salt, or cyanamide. 48 hours after drug treatment, cell lysates were prepared and subjected to immunoblotting with a tyrosinase and ERK antibody. Similar protocols were utilized in primary melanocytes. Melanocytes were plated in 96 well microtiter plate in the presence of drug or vehicle. 24 hours after drug treatment, melanocytes were treated with UV. Cell lysates were prepared 24 hours after UV treatment and subjected to immunoblotting. In order to measure an impact of cyanamide on pigment production in melanocytes, primary melanocytes were incubated in the presence of vehicle, phenylthiourea, or increasing concentrations of cyanamide. Cells were incubated for an additional 7 days, with one media change on day 4, prior to collection of absorbance and viability values. For bafilomycin experiments, MNT-1 cells were transfected with 75 nM siRNA in 12 well plates. 80 hours after transfection, 25 nM bafilomycin was added. 96 hours after transfection cell lysates were prepared and subjected to immunoblotting.

Immunofluorescence

For immunoflourescence detection of melanosome and autophagy markers, cells were fixed in 2% paraformaldehyde for 1 hour. Coverslips were washed in PBS, cells were permeabilized with 0.1% Triton-X-100 (MNT-1 cells) or saponin (primary melanocytes), and blocked in 1% BSA with 0.1% Tween 20. Cells were incubated with primary antibodies (Pmel17, LC3-b, Apg5) for 1 hour followed by incubation with secondary antibody for 1 hour. Confocal images were acquired using a LSM-510 meta two photon microscope.

Immunohistochemistry.

Mouse skin sections from four wild type and four beclin 1 haploinsufficient mice were fixed in formalin and paraffin embedded. Haematoxylin and eosin staining were performed following standard protocols. Melanin was stained using the Masson-Fontana technique with a neutral red counterstain.(Stevens 1996) S100 staining was performed as described using an eosin counterstain.(Zhu et al. 2002)

REFERENCES

Ando H, Kondoh H, Ichihashi M, Hearing V J (2007) Approaches to identify inhibitors of melanin biosynthesis via the quality control of tyrosinase. J Invest Dermatol 127(4): 751-761.

Barsh G S (2003) What controls variation in human skin color? PLoS Biol 1(1): E27.

Bennett D C, Lamoreux M L (2003) The color loci of mice—a genetic century. Pigment Cell Res 16(4): 333-344.

Cen D, Gonzalez R I, Buckmeier J A, Kahlon R S, Tohidian N B et al. (2002) Disulfiram induces apoptosis in human melanoma cells: a redox-related process. Mol Cancer Ther 1(3): 197-204. Costin G E, Hearing V J (2007) Human skin pigmentation: melanocytes modulate skin color in response to stress. Faseb J 21(4): 976-994.

Dell'Angelica E C (2003) Melanosome biogenesis: shedding light on the origin of an obscure organelle. Trends Cell Biol 13(10): 503-506.

DeMaster E G, Redfern B, Nagasawa H T (1998) Mechanisms of inhibition of aldehyde dehydrogenase by nitroxyl, the active metabolite of the alcohol deterrent agent cyanamide. Biochem Pharmacol 55 (12): 2007-2015.

Di Pietro S M, Falcon-Perez J M, Tenza D, Setty S R, Marks M S et al. (2006) BLOC-1 interacts with BLOC-2 and the AP-3 complex to facilitate protein trafficking on endosomes. Molecular biology of the cell 17(9): 4027-4038.

Edenberg H J (2007) The genetics of alcohol metabolism: role of alcohol dehydrogenase and aldehyde dehydrogenase variants. Alcohol Res Health 30(1): 5-13.

Fedorow H, Tribl F, Halliday G, Gerlach M, Riederer P et al. (2005) Neuromelanin in human dopamine neurons: comparison with peripheral melanins and relevance to Parkinson's disease. Progress in neurobiology 75(2): 109-124.

Garraway L A, Widlund H R, Rubin M A, Getz G, Berger A J et al. (2005) Integrative genomic analyses identify MITF as a lineage survival oncogene amplified in malignant melanoma. Nature 436 (7047): 117-122.

Hall A M, Orlow S J (2005) Degradation of tyrosinase induced by phenylthiourea occurs following Golgi maturation. Pigment Cell Res 18(2): 122-129.

Hoek K, Rimm D L, Williams K R, Zhao H, Ariyan S et al. (2004) Expression profiling reveals novel pathways in the transformation of melanocytes to melanomas. Cancer research 64(15): 5270-5282.

Kim Y J, Uyama H (2005) Tyrosinase inhibitors from natural and synthetic sources: structure, inhibition mechanism and perspective for the future. Cell Mol Life Sci 62(15): 1707-1723.

Kobayashi T, Urabe K, Orlow S J, Higashi K, Imokawa G et al. (1994) The Pmel 17/silver locus protein. Characterization and investigation of its melanogenic function. J Biol Chem 269(46): 29198-29205.

Kushimoto T, Basrur V, Valencia J, Matsunaga J, Vieira W D et al. (2001) A model for melanosome biogenesis based on the purification and analysis of early melanosomes. Proceedings of the National Academy of Sciences of the United States of America 98(19): 10698-10703.

Lamason R L, Mohideen M A, Mest J R, Wong A C, Norton H L et al. (2005) SLC24A5, a putative cation exchanger, affects pigmentation in zebrafish and humans. Science 310(5755): 1782-1786.

Levitt J (2007) The safety of hydroquinone: a dermatologist's response to the 2006 Federal Register. J Am Acad Dermatol 57(5): 854-872.

Levy C, Khaled M, Fisher D E (2006) MITF: master regulator of melanocyte development and melanoma oncogene. Trends Mol Med 12(9): 406-414.

Malo N, Hanley J A, Cerquozzi S, Pelletier J, Nadon R (2006) Statistical practice in high-throughput screening data analysis. Nat Biotechnol 24(2): 167-175.

Proikas-Cezanne T, Waddell S, Gaugel A, Frickey T, Lupas A et al. (2004) WIPI-1alpha (WIPI49), a member of the novel 7-bladed WIPI protein family, is aberrantly expressed in human cancer and is linked to starvation-induced autophagy. Oncogene 23(58): 9314-9325.

Qu X, Yu J, Bhagat G, Furuya N, Hibshoosh H et al. (2003) Promotion of tumorigenesis by heterozygous disruption of the beclin 1 autophagy gene. The Journal of clinical investigation 112 (12): 1809-1820.

Raposo G, Marks M S (2007) Melanosomes—dark organelles enlighten endosomal membrane transport. Nature reviews 8(10): 786-797.

Raposo G, Marks M S, Cutler D F (2007) Lysosome-related organelles: driving post-Golgi compartments into specialisation. Current opinion in cell biology 19(4): 394-401.

Sarangarajan R, Apte S P (2005) Melanization and phagocytosis: implications for age related macular degeneration. Molecular vision 11: 482-490.

Slominski A, Tobin D J, Shibahara S, Wortsman J (2004) Melanin pigmentation in mammalian skin and its hormonal regulation. Physiol Rev 84(4): 1155-1228.

Smit N P, Van der Meulen H, Koerten H K, Kolb R M, Mommaas A M et al. (1997) Melanogenesis in cultured melanocytes can be substantially influenced by L-tyrosine and L-cysteine. The Journal of investigative dermatology 109(6): 796-800.

Smit N P, Kolb R M, Lentjes E G, Noz K C, van der Meulen H et al. (1998) Variations in melanin formation by cultured melanocytes from different skin types. Archives of dermatological research 290(6): 342-349.

Stevens A, Chalk B T (1996) Pigments and Minerals. In: J D Bancroft and A Stevens, Editors, Theory and Practical Histological Techniques: 243-267.

Sulem P, Gudbjartsson D F, Stacey S N, Helgason A, Rafnar T et al. (2007) Genetic determinants of hair, eye and skin pigmentation in Europeans. Nat Genet 39(12): 1443-1452.

Tachibana M (1999) Sound needs sound melanocytes to be heard. Pigment cell research/sponsored by the European Society for Pigment Cell Research and the International Pigment Cell Society 12 (6): 344-354.

Theos A C, Truschel S T, Tenza D, Hurbain I, Harper D C et al. (2006) A lumenal domain-dependent pathway for sorting to intralumenal vesicles of multivesicular endosomes involved in organelle morphogenesis. Developmental cell 10(3): 343-354.

Theos A C, Tenza D, Martina J A, Hurbain I, Peden A A et al. (2005) Functions of adaptor protein (AP)-3 and AP-1 in tyrosinase sorting from endosomes to melanosomes. Molecular biology of the cell 16 (11): 5356-5372.

Watabe H, Valencia J C, Yasumoto K, Kushimoto T, Ando H et al. (2004) Regulation of tyrosinase processing and trafficking by organellar pH and by proteasome activity. The Journal of biological chemistry 279(9): 7971-7981.

Whitehurst A W, Bodemann B O, Cardenas J, Ferguson D, Girard L et al. (2007) Synthetic lethal screen identification of chemosensitizer loci in cancer cells. Nature 446(7137): 815-819.

Zecca L, Zucca F A, Albertini A, Rizzio E, Fariello R G (2006) A proposed dual role of neuromelanin in the pathogenesis of Parkinson's disease. Neurology 67(7 Suppl 2): S8-11.

Zhu Y, Ghosh P, Charnay P, Burns D K, Parada L F (2002) Neurofibromas in NF1: Schwann cell origin and role of tumor environment. Science (New York, N.Y. 296(5569): 920-922.

What is claimed is:

1. A topical formulation for reducing skin pigmentation, the formulation comprising cyanamide in an amount ranging from 50 µM to 500 µM.

2. The topical formulation of claim 1, wherein the formulation is a cream.

3. The topical formulation of claim 1, wherein the formulation is an ointment.

4. The topical formulation of claim 1, wherein the formulation is a paste.

5. The topical formulation of claim 1, wherein the formulation is a lotion.

6. The topical formulation of claim 1, wherein the formulation is a gel.

7. The topical formulation of claim 1, wherein the formulation is a solution.

8. The topical formulation of claim 1, wherein the amount of cyanamide is in a range from 100 µM to 500 µM.

* * * * *